US011197636B2

(12) United States Patent
Wagner et al.

(10) Patent No.: US 11,197,636 B2
(45) Date of Patent: Dec. 14, 2021

(54) STABILIZED SENSOR MODULES AND MONITORING DEVICES INCORPORATING SAME

(71) Applicant: VALENCELL, INC., Raleigh, NC (US)

(72) Inventors: Wolfgang Wagner, Chapel Hill, NC (US); Steven Matthew Just, Cary, NC (US); Jonathan T. Walter, Wake Forest, NC (US); Jesse Berkley Tucker, Youngsville, NC (US); Steven Francis Leboeuf, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 684 days.

(21) Appl. No.: 15/554,158

(22) PCT Filed: Feb. 23, 2016

(86) PCT No.: PCT/US2016/019114
§ 371 (c)(1),
(2) Date: Aug. 28, 2017

(87) PCT Pub. No.: WO2016/140835
PCT Pub. Date: Sep. 9, 2016

(65) Prior Publication Data
US 2018/0078209 A1   Mar. 22, 2018

Related U.S. Application Data
(60) Provisional application No. 62/127,624, filed on Mar. 3, 2015.

(51) Int. Cl.
*A61B 5/00* (2006.01)
*A61B 5/1455* (2006.01)
(Continued)

(52) U.S. Cl.
CPC .......... *A61B 5/6844* (2013.01); *A61B 5/0013* (2013.01); *A61B 5/0261* (2013.01);
(Continued)

(58) Field of Classification Search
CPC . A61B 5/6844; A61B 5/0013; A61B 5/02427; A61B 5/0261; A61B 5/6803;
(Continued)

(56) References Cited

U.S. PATENT DOCUMENTS 5,938,590 A    8/1999   Elliott
8,308,641 B2   11/2012  Moroney, III et al.
(Continued)

FOREIGN PATENT DOCUMENTS

JP   2014-68733       4/2014
KR   20-0204510 Y1   11/2000
(Continued)

OTHER PUBLICATIONS

Communication with Supplementary European Search Report, EP Patent Application No. 16759275.7, dated Feb. 15, 2018, 9 pp.
(Continued)

*Primary Examiner* — Sanjay Cattungal
(74) *Attorney, Agent, or Firm* — Myers Bigel, P.A.

(57) ABSTRACT

A sensor module includes a housing and a sensor assembly disposed within the housing. The sensor assembly includes a base having at least one energy emitter and at least one energy detector, and a guide layer overlying the base in face-to-face relationship. The guide layer has at least one protrusion extending outwardly to accommodate the at least one energy emitter, and a plurality of outwardly extending stabilizing members. The housing has at least one first opening through which the at least one protrusion extends, and a plurality of second openings through which the stabilizing members extend. Some of the stabilizing mem-
(Continued)

bers have an outwardly extending length that is greater than an outwardly extending length of the at least one protrusion. Some of the stabilizing members are substantially cylindrical and have a circular cross-sectional profile, and some of the stabilizing members are partially cylindrical and have a partially circular cross-sectional profile.

17 Claims, 28 Drawing Sheets

(51) Int. Cl.
    *A61B 5/024*      (2006.01)
    *A61B 5/026*      (2006.01)

(52) U.S. Cl.
    CPC ...... *A61B 5/02427* (2013.01); *A61B 5/14552* (2013.01); *A61B 5/6803* (2013.01); *A61B 5/6804* (2013.01); *A61B 5/6817* (2013.01); *A61B 5/721* (2013.01); *A61B 2562/0238* (2013.01); *A61B 2562/046* (2013.01); *A61B 2562/146* (2013.01); *A61B 2562/228* (2013.01)

(58) Field of Classification Search
    CPC ... A61B 5/6804; A61B 5/721; A61B 5/14552; A61B 5/6817; A61B 2562/0238; A61B 2562/046; A61B 2562/146; A61B 2562/228

See application file for complete search history.

(56) References Cited

U.S. PATENT DOCUMENTS

| | | | |
|---|---|---|---|
| 10,542,893 B2 | 1/2020 | Leboeuf et al. | |
| 2005/0209516 A1 | 9/2005 | Fraden | |
| 2007/0036383 A1 | 2/2007 | Romero | |
| 2009/0177097 A1 | 7/2009 | Ma et al. | |
| 2010/0217098 A1* | 8/2010 | LeBoeuf | A61B 5/0084 600/301 |
| 2010/0249554 A1 | 9/2010 | McKenna et al. | |
| 2011/0121082 A1 | 5/2011 | Phaneuf | |
| 2011/0130638 A1 | 6/2011 | Raridan, Jr. | |
| 2011/0257521 A1 | 10/2011 | Fraden | |
| 2012/0101602 A1 | 4/2012 | Andren et al. | |
| 2013/0131519 A1* | 5/2013 | LeBoeuf | A61B 5/0059 600/476 |
| 2013/0245488 A1 | 9/2013 | Quinn et al. | |
| 2013/0267854 A1* | 10/2013 | Johnson | A61B 5/0064 600/473 |
| 2014/0005557 A1 | 1/2014 | Rich et al. | |
| 2014/0100432 A1 | 4/2014 | Golda et al. | |
| 2014/0107493 A1* | 4/2014 | Yuen | A61B 5/0002 600/473 |
| 2014/0228721 A1 | 8/2014 | Ehrenreich et al. | |
| 2014/0266939 A1* | 9/2014 | Baringer | A61B 5/02416 343/729 |
| 2014/0275850 A1* | 9/2014 | Venkatraman | G01S 19/19 600/301 |
| 2014/0276014 A1 | 9/2014 | Khanicheh et al. | |
| 2014/0323880 A1 | 10/2014 | Ahmed et al. | |
| 2014/0378844 A1 | 12/2014 | Fei | |
| 2015/0025355 A1 | 1/2015 | Bailey et al. | |
| 2015/0057511 A1 | 2/2015 | Basu | |
| 2015/0057512 A1 | 2/2015 | Kapoor | |
| 2016/0061726 A1 | 3/2016 | Ness et al. | |
| 2017/0325744 A1 | 11/2017 | Allec et al. | |

FOREIGN PATENT DOCUMENTS

| | | | |
|---|---|---|---|
| WO | WO 2014/092932 A1 | 6/2014 | |
| WO | WO 2014/116942 A2 | 7/2014 | |

OTHER PUBLICATIONS

International Search Report and Written Opinion of the International Searching Authority, International Patent Application No. PCT/US2016/019114 (16 pages) (dated Jul. 26, 2016).

International Preliminary Report on Patentability, International Patent Application No. PCT/US2016/019114 (9 pages) (dated Jun. 5, 2017).

International Search Report and Written Opinion of the International Searching Authority, International Patent Application No. PCT/US2016/019126 (12 pages) (dated May 26, 2016).

International Preliminary Report on Patentability, International Patent Application No. PCT/US2016/019126 (6 pages) (dated Jun. 5, 2017).

International Search Report and Written Opinion of the International Searching Authority, International Patent Application No. PCT/US2016/019132 (9 pages) (dated May 26, 2016).

International Preliminary Report on Patentability, International Patent Application No. PCT/US2016/019132 (3 pages) (dated Jun. 5, 2017).

"Communication pursuant to Article 94(3) EPC", EP Application No. 16759275.7, dated Nov. 30, 2020, 8 pp.

* cited by examiner

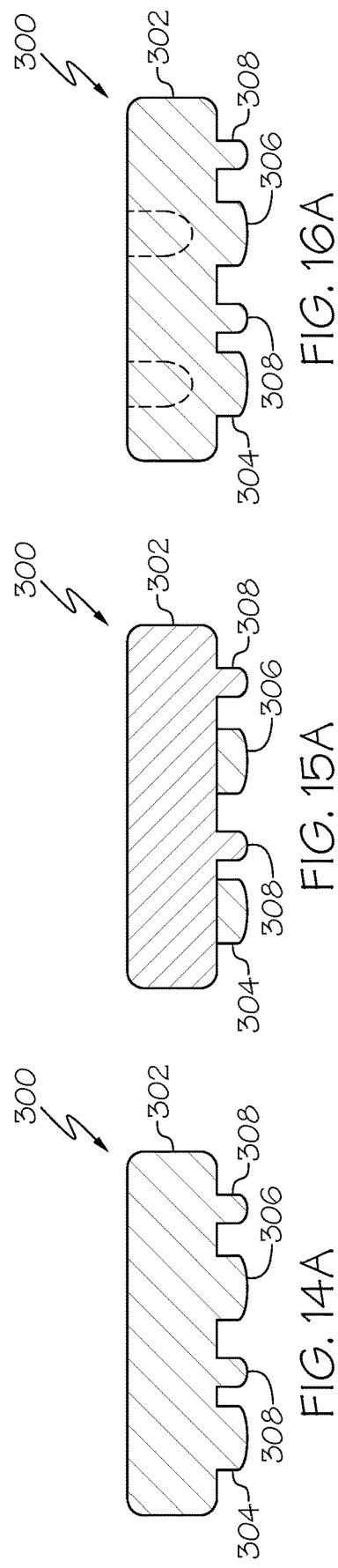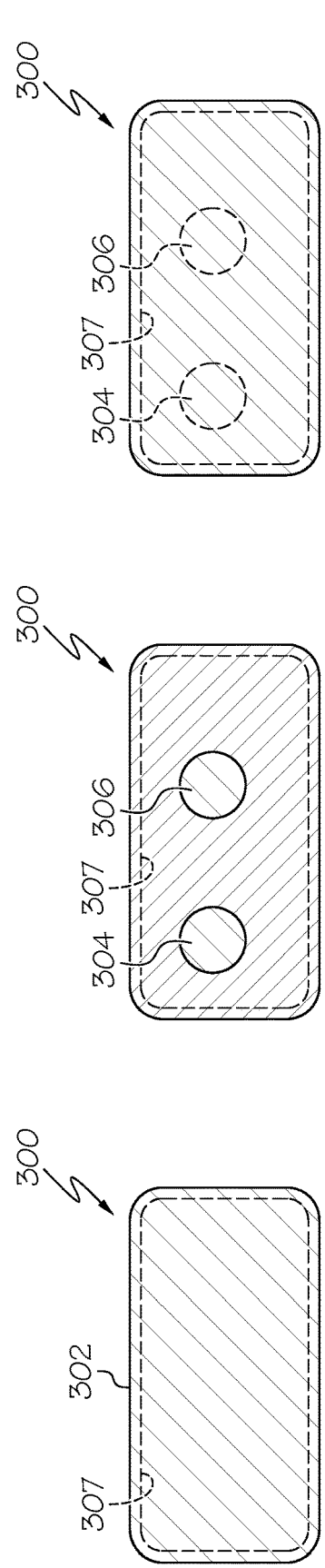

STABILIZED SENSOR MODULES AND MONITORING DEVICES INCORPORATING SAME

RELATED APPLICATIONS

This application is a 35 U.S.C. § 371 national stage application of PCT Application No. PCT/US2016/019114, filed on Feb. 23, 2016, which itself claims the benefit of and priority to U.S. Provisional Patent Application No. 62/127, 624 filed Mar. 3, 2015, the disclosures of which are incorporated herein by reference as if set forth in their entireties. The above-referenced PCT International Application was published in the English language as International Publication No. WO 2016/140835 A1 on Sep. 9, 2016.

FIELD OF THE INVENTION

The present invention relates generally to monitoring devices and, more particularly, to monitoring devices for measuring physiological information.

BACKGROUND OF THE INVENTION

Photoplethysmography (PPG) is based upon shining light into the human body and measuring how the scattered light intensity changes with each pulse of blood flow. The scattered light intensity will change in time with respect to changes in blood flow, blood vessels, or blood opacity associated with heart beats, breaths, blood oxygen level ($SpO_2$), and the like. Such a sensing methodology may require the magnitude of light energy reaching the volume of flesh being interrogated to be steady and consistent so that small changes in the quantity of scattered photons can be attributed to varying blood flow. If the incidental and scattered photon count magnitude changes due to light coupling variation between the source or detector and the skin surface, then the signal of interest can be difficult to ascertain due to large photon count variability caused by loss or variation of optical coupling. Changes in the surface area (and volume) of skin being impacted with photons, or varying skin surface curvature reflecting significant portions of the photons, may also significantly impact optical coupling efficiency. Physical activity, such a walking, cycling, running, etc., may cause motion artifacts in the optical scatter signal from the body, and time-varying changes in photon intensity due to motion artifacts may swamp-out time-varying changes in photon intensity due to blood flow changes. Each of these changes in optical coupling can affect the photonic interrogation count by a large percent of the total photon count and diminish the quality of the signal of interest, with lower probability of obtaining accurate values of desired data.

An earbud is a good choice for incorporation of a photoplethysmograph device because it is a form factor that individuals are familiar with, it is a device that is commonly worn for long periods of time, and it frequently is used during exercise which is a time when individuals may benefit most from having accurate heart rate data (or other physiological data). Unfortunately, incorporation of a photoplethysmograph device into an earbud poses several challenges. For example, earbuds may be uncomfortable to wear for long periods of time, particularly if they deform the ear surface. Moreover, human ear anatomy may vary significantly from person to person, so finding an earbud form that will fit comfortably in many ears may pose significant challenges. In addition, earbuds made for vigorous physical activity typically incorporate an elastomeric surface and/or elastomeric features to function as springs that dampen earbud acceleration within the ear. Although, these features may facilitate retention of an earbud within an ear during high acceleration and impact modalities, they do not adequately address optical skin coupling requirements needed to achieve quality photoplethysmography.

Conventional photoplethysmography devices, as illustrated for example in FIGS. 1A-1C, typically suffer from reduced skin coupling as a result of subject motion. For example, most conventional photoplethysmography devices use a spring to clip the sensor onto either an earlobe (FIG. 1A) or a fingertip (FIG. 1B). Unfortunately, these conventional devices tend to have a large mass and may not maintain consistent skin contact when subjected to large accelerations, such as when a subject is exercising.

A conventional earbud device that performs photoplethysmography in the ear is the MX-D100 player from Perception Digital of Wanchai, Hong Kong (www.perceptiondigital.com). This earbud device, illustrated in FIG. 1C and indicated as 10, incorporates a spring 12 to improve PPG signal quality. However, the spring 12 forcibly presses the entire earbud 10 within the ear E of a subject to minimize motion of the entire earbud 10. There are several drawbacks to the device 10 of FIG. 1C. For example, the source/sensor module is coupled to the entire earbud mass and, as such, may experience larger translation distances resulting in greater signal variability when the ear undergoes accelerations. In addition, because the earbud 10 is held in place with one primary spring force direction, significant discomfort can be experienced by the end user. Moreover, the earbud motion may only be constrained in one direction due to the single spring force direction.

Another conventional wearable monitoring device is illustrated in FIGS. 2A-2C. The monitoring device 200 includes a housing 210 having a screen 220 attached to a band B that is configured to be secured around an appendage of a subject. The housing 210 includes a portion 210a with a biometric sensor 212 that is wearably positionable adjacent the skin of a subject. The biometric sensor 212 includes one or more optical emitters 214 and one or more optical detectors 216 (FIG. 2B). As illustrated in FIG. 2C, the biometric sensor 212 does not extend outwardly from the housing portion 210a. Unfortunately, wearable devices such as illustrated in FIGS. 2A-2C may not maintain consistent skin contact with the sensor 212 when the device is subjected to large accelerations, such as when a subject is exercising.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a sensor module includes a housing and a sensor assembly disposed within the housing. The sensor assembly includes a base having at least one energy emitter and at least one energy detector, and a guide layer overlying the base in face-to-face relationship. The guide layer has at least one protrusion that serves as an energy guide extending outwardly to accommodate the at least one energy emitter, and a plurality of outwardly extending stabilizing members. The housing has at least one first opening through which the at least one protrusion extends, and a plurality of second openings through which the stabilizing members extend. The housing may be formed of substantially opaque material.

In some embodiments, the housing is configured to removably receive a fastener for securing the sensor module to a wearable article, such as an earbud, an armband, a wristband, a legband, a neckband, a ring, jewelry, glasses, headgear, a safety strap, a helmet, a patch, a tattoo, an earring, an article of clothing, etc. In some embodiments, the housing includes a first magnet configured to removably secure the sensor module to a wearable article via a second magnet. Other types of fasteners may be utilized, however, such as hook and loop fasteners, etc.

The at least one energy emitter is configured to direct electromagnetic radiation, mechanical energy, acoustical energy, electrical energy, and/or thermal energy, and the at least one energy detector is configured to detect electromagnetic radiation, mechanical energy, acoustical energy, electrical energy, and/or thermal energy. In some embodiments, the at least one energy emitter is one or more optical emitters and the at least one energy detector is one or more optical detectors.

In embodiments where the at least one energy detector is an optical detector, the sensor module may further include a lens that overlies and is in optical communication with the optical detector. The guide layer includes an opening configured to accommodate the lens, and the housing includes a third opening through which the lens extends. In other embodiments, the guide layer includes at least one protrusion extending outwardly to accommodate the at least one optical detector and to serve as a light guide for directing light to the optical detector. Each protrusion associated with an optical emitter is in optical communication with the respective optical emitter and serves as a light guide directing light into the skin of a subject.

In some embodiments, at least one coupler is associated with the at least one energy emitter and/or the at least one energy detector. An exemplary coupler includes, but is not limited to, a lens, an electrode, a thermally conductive electrode, a piezoelectric element, or a rigid element. Such couplers may enhance and/or facilitate the transfer of energy from an emitter and to a detector.

It should be noted that a variety of energy emitter and energy detectors may be generally used within embodiments of the present invention. In such case the stabilizers may be essentially identical to that used for the case of optical emitters and optical detectors, but the protrusions (energy guiding protrusions) may be substantially different. For example, for the case where the energy emitter is a thermal emitter, the emitter and detector protrusions may comprise a core of thermally conductive material (i.e., metals, metallics, conducting polymer materials, nanostructured materials, and the like) and a cladding of thermally insulating material (i.e., insulating polymers, insulating plastics, rubber, insulating polycarbonate, acrylic, insulating glass, etc.) that serve as couplers. For the case where electrical emitters and detectors are used, the emitter and detector protrusions may comprise a core of electrically conductive material and a cladding of electrically insulating material that serve as couplers. In the case of a mechanical emitter (such as a piezoelectric actuator) and mechanical detector, the emitter and detector protrusions may be comprised of a mechanically rigid material and a cladding of mechanically resilient material that serve as couplers. In all of these cases, cladding may not be critical for biometric sensing functionality, but may be supportive by directing energy transmission through the desired pathway between the body of the person and the emitter/detector. Moreover, a variety of electrically conductive materials, mechanically rigid materials, resilient materials, etc. may be used as is well-known to those skilled in the art.

In some embodiments, one or more of the stabilizing members has an outwardly extending length that is greater than an outwardly extending length of the at least one protrusion.

In some embodiments, at least some of the stabilizing members are substantially cylindrical and have a substantially circular cross-sectional profile, and at least some of the stabilizing members are partially cylindrical and have a partially circular cross-sectional profile.

In some embodiments, one or more of the stabilizing members have a distal end with a rounded configuration.

In some embodiments, one or more of the stabilizing members have a distal end with a textured configuration, such as a plurality of raised bumps.

In some embodiments, one or more of the stabilizing members have a distal end with a plurality of teeth.

In some embodiments, the stabilizing members are arranged in a pattern. However, in other embodiments, the stabilizing members may have a somewhat random arrangement. Typically, at least one stabilizing member is located near each protrusion to facilitate stabilization of the protrusion relative to the skin of a subject wearing the sensor module.

In some embodiments, the guide layer, stabilizing members, and protrusions are formed from the same or similar material, such as silicone, polycarbonate, glass, and acrylic. Typically the protrusions and stabilizing members are formed from a resilient material.

In some embodiments, the at least one protrusion is substantially cylindrical.

In some embodiments, the sensor module includes a signal processor configured to receive and process signals produced by the at least one detector, and may also include a motion sensor configured to detect motion of the sensor module. The motion sensor may be, for example, an inertial sensor, a piezoelectric sensor, an optical sensor, etc. In some embodiments, the motion sensor may be a photoplethysmography (PPG) sensor used for measuring blood flow.

According to other embodiments of the present invention, a sensor module includes a housing and a sensor assembly disposed within the housing. The sensor assembly includes a base having at least one optical emitter and at least one optical detector, and a guide layer overlying the base in face-to-face relationship. The guide layer has at least one protrusion extending outwardly to accommodate the at least one optical emitter, and has a plurality of outwardly extending stabilizing members. The at least one protrusion is in optical communication with the at least one optical emitter and serves as a light guide directing light into the skin of a subject. In some embodiments, the stabilizing members each have an outwardly extending length that is greater than an outwardly extending length of the at least one protrusion.

The housing includes at least one first opening through which the at least one protrusion extends, and a plurality of second openings through which the stabilizing members extend. The housing may be formed of substantially opaque material. In some embodiments, the housing is configured to removably receive a fastener for securing the sensor module to a wearable article, such as an earbud, an armband, a wristband, a legband, a neckband, a ring, jewelry, glasses, headgear, a patch, a tattoo, an earring, or an article of clothing. In some embodiments, the housing includes a first magnet configured to removably secure the sensor module to a wearable article via a second magnet.

In some embodiments, the guide layer includes at least one protrusion extending outwardly to accommodate the at least one optical detector. In other embodiments, the sensor module includes a lens that overlies and is in optical communication with the at least one optical detector. The guide layer has an opening that is configured to accommodate the lens, and the housing has a third opening through which the lens extends.

In some embodiments, the sensor module includes a signal processor configured to receive and process signals produced by the at least one optical detector, and may also include a motion sensor configured to detect motion of the sensor module. The motion sensor may be, for example, an inertial sensor, a piezoelectric sensor, an optical sensor, etc. In some embodiments, the motion sensor may be a photoplethysmography (PPG) sensor used for measuring blood flow.

According to other embodiments of the present invention, a monitoring device includes a band configured to be secured around an appendage of a subject, and a sensor module secured to the band via supporting material. The band is formed of material having a first Durometer value, and the supporting material has a second Durometer value that is lower than the first Durometer value, thus acting as a suspension region for the sensor module. In some embodiments, the supporting material extends substantially around a periphery of the sensor module. In other embodiments, the supporting material substantially surrounds the sensor module.

The sensor module includes a housing and a sensor assembly disposed within the housing. The sensor assembly includes a base having at least one energy emitter and at least one energy detector. A guide layer overlies the base in face-to-face relationship and includes at least one protrusion extending outwardly to accommodate the at least one energy emitter, and a plurality of outwardly extending stabilizing members. The housing includes at least one first opening through which the at least one protrusion extends, and a plurality of second openings through which the stabilizing members extend.

The at least one energy emitter is configured to direct electromagnetic radiation, mechanical energy, acoustical energy, electrical energy, and/or thermal energy, and the at least one energy detector is configured to detect electromagnetic radiation, mechanical energy, acoustical energy, electrical energy, and/or thermal energy. In some embodiments, the at least one energy emitter comprises at least one optical emitter and the at least one energy detector comprises at least one optical detector.

According to other embodiments of the present invention, a monitoring device includes a first housing that is configured to be removably secured to a wearable article, and a sensor module secured to the first housing via supporting material. The first housing is formed from material having a first Durometer value, and the supporting material has a second Durometer value that is lower than the first Durometer value, thus acting as a suspension region for the sensor module. In some embodiments, the supporting material extends substantially around a periphery of the sensor module. In other embodiments, the supporting material substantially surrounds the sensor module.

The first housing is configured to receive a fastener and is configured to be removably secured to a wearable article, such as an earbud, an armband, a wristband, a legband, a neckband, a ring, jewelry, glasses, headgear, a patch, a tattoo, an earring, or an article of clothing, via the fastener. In some embodiments, the first housing includes a first magnet and is configured to be removably secured to a wearable article via a second magnet.

The sensor module includes a second housing and a sensor assembly disposed within the second housing. The sensor assembly includes a base having at least one energy emitter and at least one energy detector, and a guide layer that overlies the base in face-to-face relationship. The guide layer includes at least one protrusion extending outwardly to accommodate the at least one energy emitter, and a plurality of outwardly extending stabilizing members. The second housing includes at least one first opening through which the at least one protrusion extends, and a plurality of second openings through which the stabilizing members extend.

The at least one energy emitter is configured to direct electromagnetic radiation, mechanical energy, acoustical energy, electrical energy, and/or thermal energy, and wherein the at least one energy detector is configured to detect electromagnetic radiation, mechanical energy, acoustical energy, electrical energy, and/or thermal energy. In some embodiments, the at least one energy emitter comprises at least one optical emitter and the at least one energy detector comprises at least one optical detector.

According to other embodiments of the present invention, an earbud cover configured to be removably attached to, and at least partially cover, an audio earbud includes at least one light guide that is configured to guide light from at least one optical emitter associated with the audio earbud to a region of a body of a subject wearing the audio earbud and/or guide light from the body of the subject to at least one optical detector associated with the audio earbud. The earbud cover also includes a plurality of stabilizing members extending outwardly from an outer surface of the cover adjacent the at least one light guide. The stabilizing members are typically formed from a resilient material.

In some embodiments, at least some of the stabilizing members are substantially cylindrical and have a substantially circular cross-sectional profile, and at least some of the stabilizing members are partially cylindrical and have a partially circular cross-sectional profile.

In some embodiments, one or more of the stabilizing members have a distal end with a rounded configuration.

In some embodiments, one or more of the stabilizing members have a distal end with a textured configuration, such as a plurality of raised bumps.

In some embodiments, one or more of the stabilizing members have a distal end with a plurality of teeth.

In some embodiments, the stabilizing members are arranged in a pattern. However, in other embodiments, the stabilizing members may have a somewhat random arrangement.

In some embodiments, the earbud cover includes at least one optically opaque region at least partially surrounding the at least one light guide.

In some embodiments, the earbud cover comprises plastic, polymer, or silicone, and the at least one light guide comprises plastic, polymer, silicone, acrylic, glass, polycarbonate, or an optically filtering material.

According to other embodiments of the present invention, a wearable apparatus configured to be worn against the skin of a subject is configured to measure one or more biometric parameters from the subject. The wearable apparatus includes at least one optical emitter, at least one optical detector, at least one first stabilizing member in proximity to the optical emitter; and at least one second stabilizing member in proximity to the optical detector. The wearable apparatus may be an earbud, an armband, a wristband, a legband, a neckband, a ring, jewelry, glasses, headgear, a patch, a tattoo, an earring, or an article of clothing.

The at least one first and second stabilizing members are configured to contact the skin of the user and stabilize movement of the at least one emitter and the at least one detector relative to the skin. The at least one optical emitter and at least one optical detector are supported by a base. In some embodiments, the at least one first stabilizing member has an outwardly extending length that is greater than a height of the at least one optical emitter relative to the base, and the at least one second stabilizing member has an outwardly extending length that is greater than a height of the at least one optical detector relative to the base.

According to other embodiments of the present invention, an optical adapter is configured to be removably secured to a wearable monitoring device, such as a third party monitoring device. The monitoring device includes a housing having a portion with a biometric sensor that is wearably positionable adjacent the skin of a subject. The biometric sensor includes an optical emitter and an optical detector. The optical adapter includes a base that is configured to be removably secured to the housing portion. The optical adapter includes a first light guide extending outwardly from the base that is in optical communication with the optical emitter when the base is secured to the housing portion, and a second light guide extending outwardly from the base that is in optical communication with the optical detector when the base is secured to the housing portion. The optical adapter also includes a plurality of stabilizing members extending outwardly from the base. The stabilizing members typically are formed from a resilient material.

The first light guide includes a distal end that is configured to engage a portion of a body of the subject and to deliver light from the optical emitter directly into the body of the subject. The second light guide includes a distal end that is configured to engage a portion of the body of the subject and is configured to collect light directly from the body of the subject via the distal end thereof and deliver collected light to the optical detector. In some embodiments, the first and second light guides are formed from elastomeric light transmissive material.

In some embodiments, the base, first and second light guides, and stabilizing members are formed from the same or similar material, such as silicone, polycarbonate, glass, and acrylic.

In some embodiments, the base is adhesively secured to the housing portion of the monitoring device.

In other embodiments, the base includes at least one male connector that is configured to engage at least one female connector associated with the housing portion of the monitoring device. In other embodiments, the base includes at least one female connector that is configured to engage at least one male connector associated with the housing portion of the monitoring device.

In some embodiments, stabilizing member has an outwardly extending length from the base that is greater than an outwardly extending length of the first and second light guides from the base.

In some embodiments, at least some of the stabilizing members are substantially cylindrical and have a substantially circular cross-sectional profile, and at least some of the stabilizing members are partially cylindrical and have a partially circular cross-sectional profile.

In some embodiments, one or more of the stabilizing members have a distal end with a rounded configuration.

In some embodiments, one or more of the stabilizing members have a distal end with a textured configuration, such as a plurality of raised bumps.

In some embodiments, one or more of the stabilizing members have a distal end with a plurality of teeth.

In some embodiments, the stabilizing members are arranged in a pattern. However, in other embodiments, the stabilizing members may have a somewhat random arrangement.

According to other embodiments of the present invention, a monitoring device includes a band configured to be secured to an appendage of a subject. The band includes segments separated by mechanical stress-relieving components. A biometric sensor is secured to the band so as to be wearably positionable adjacent the skin of a subject. In some embodiments, the biometric sensor includes an optical emitter and an optical detector.

According to other embodiments of the present invention, an earpiece configured to be positioned within an ear canal of a subject includes a housing, a sensor assembly disposed within the housing, and a cover removably secured to a free end of the housing. The sensor assembly includes at least one optical emitter and at least one optical detector. The cover includes at least one light guide configured to guide light from the at least one optical emitter and/or guide light from the ear of the subject to the at least one optical detector. The cover also includes a plurality of stabilizing members extending outwardly from an outer surface of the cover adjacent the at least one light guide. The earpiece may also include at least one ear support fitting associated with the housing that is configured to stabilize the earpiece within the ear canal. The cover may be formed from plastic, polymer, or silicone, and the at least one light guide may be formed from plastic, polymer, silicone, acrylic, glass, polycarbonate, or an optically filtering material. In some embodiments, the housing may include a signal processor configured to receive and process signals produced by the at least one optical detector, a motion sensor configured to detect motion of the earpiece, and/or a wireless transmitter configured to transmit data from the at least one optical detector to a remote device.

The stabilizing members may be arranged in a pattern or may be somewhat randomly arranged, and may be formed from resilient material. In some embodiments, at least some of the stabilizing members are substantially cylindrical and have a substantially circular cross-sectional profile, and at least some of the stabilizing members are partially cylindrical and have a partially circular cross-sectional profile. In some embodiments at least some of the stabilizing members have a distal end with a rounded configuration, a textured configuration, or a plurality of teeth.

According to other embodiments of the present invention, an earpiece configured to be positioned within an ear canal of a subject includes a housing having at least one light guide extending from a portion thereof, a sensor assembly disposed within the housing, and a cover removably secured to a free end of the housing. The sensor assembly includes at least one optical emitter and at least one optical detector, and the at least one optical emitter and/or at least one optical detector are in optical communication with the at least one light guide. The cover includes at least one aperture through which the at least one light guide can guide light from the at least one optical emitter to the ear of the subject and/or guide light from the ear of the subject to the at least one optical detector. The cover also includes a plurality of stabilizing members extending outwardly from an outer surface of the cover adjacent the at least one aperture. The earpiece may also include at least one ear support fitting associated with the housing that is configured to stabilize the earpiece within the ear canal. In some embodiments, the housing may include a signal processor configured to receive and process signals produced by the at least one optical detector, a motion sensor configured to detect motion of the earpiece, and/or a wireless transmitter configured to transmit data from the at least one optical detector to a remote device.

The stabilizing members may be arranged in a pattern or may be somewhat randomly arranged, and may be formed from resilient material. In some embodiments, at least some of the stabilizing members are substantially cylindrical and have a substantially circular cross-sectional profile, and at least some of the stabilizing members are partially cylindrical and have a partially circular cross-sectional profile. In some embodiments at least some of the stabilizing members have a distal end with a rounded configuration, a textured configuration, or a plurality of teeth.

Monitoring devices incorporating sensor modules and optical adapters, according to embodiments of the present invention, are advantageous over conventional monitoring devices for several reasons. One is comfort of fit. A monitoring device according to embodiments of the present invention may be comfortable to wear for a period of time and may provide more accurate biometrics than conventional devices. The stabilizing members associated with the sensor modules and optical adapters of the present invention allow a sensor module to stay in proximity with the interrogation area of interest, even under extreme accelerations, and may be able to continuously report useable data and offer the end-user a higher confidence level in the device's accuracy. Moreover, the stabilizing members are formed from resilient material and have a configuration and spacing that stabilizes the device around the skin region for energy interrogation (such as optical interrogation when the energy emitter is an optical emitter) without pushing away blood from the interrogation region (i.e., the skin region facing the energy emitter(s) and/or energy detector(s)).

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 14A is a side view of an optical adapter, according to some embodiments of the present invention.

FIG. 14B is a top view of the optical adapter of FIG. 14A.

FIG. 15A is a side view of an optical adapter, according to some embodiments of the present invention.

FIG. 15B is a top view of the optical adapter of FIG. 15A.

FIG. 16A is a side view of an optical adapter, according to some embodiments of the present invention.

FIG. 16B is a top view of the optical adapter of FIG. 16A.

DETAILED DESCRIPTION

Figure 1A:
FIG. 1A is a perspective view of a conventional PPG device attached to the ear of a person.
Figure 1B:
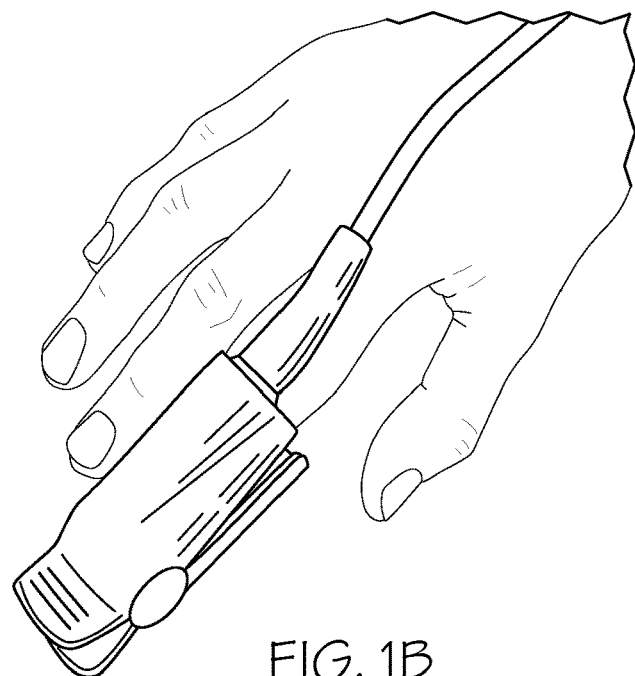
FIG. 1B is a perspective view of a conventional PPG device attached to a finger of a person.
Figure 1C:
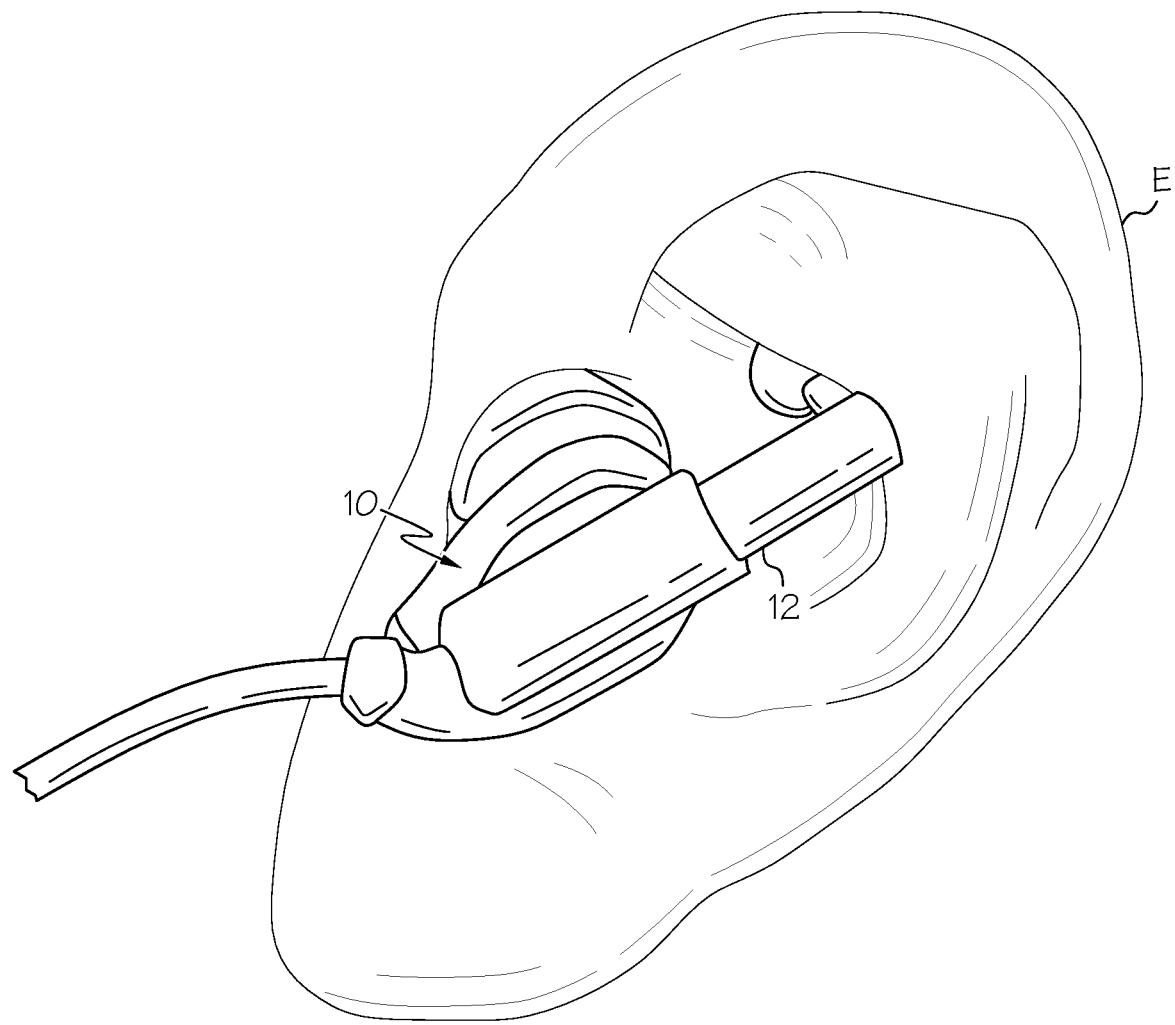
FIG. 1C illustrates a conventional PPG device attached to the ear of a person, and wherein a biasing element is utilized to retain the photoplethysmography device in the person's ear.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary by +/−twenty percent (20%).

The term "base", as used herein, may include any type of printed circuit board (PCB), substrate, or other structure that can support various types of energy emitters, energy detectors, electrical components, and/or electrical connectors.

The term "monitoring device" includes any type of device that may be attached to or near the ear, to an appendage, or other body region of a user and may have various configurations, without limitation.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "chipset" generally refers to a single integrated chip, a single integrated chip and associated electronic components, or a plurality of integrated chips that work together to perform a function. For example, an optical chipset may be a single integrated chip, a single integrated chip mounted on a circuit board with associated electronics, a plurality of integrated chips that are coupled together to collect and process optical signals, or the like. To be a "chipset", the "chips" or components may not need to be located in the same region but rather must work together to execute a function.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a monitoring device, according to embodiments of the present invention.

The term "photoplethysmography" (PPG) refers to a method of sensing, measuring, and/or assessing blood-flow related characteristics by sensing light scatter from the body. A PPG sensor may shine light upon the skin or other part of the body, sense the resulting light scatter, and generate a photoplethysmogram or other blood flow information which may then be processed by a processor to generate information about heart rate, RRi, respiration rate, blood flow, cardiac output, blood pressure, blood hydration (osmality), $VO_2$, blood analyte levels (such as blood oxygenation level, the concentration of various types of hemoglobin, bilirubin levels, cholesterol levels, and the like), and other blood flow-related characteristics. A plurality of optical wavelengths may be used in PPG, and a plurality of different optical sources and optical detectors may be used. In some embodiments, the method of sensing, measuring, and/or assessing blood-flow related characteristics may comprise attenuating noise artifacts (such as motion-artifacts and/or environmental-artifacts) from the scattered light information via analog signal processing and/or digital signal processing.

In the following figures, various monitoring devices will be illustrated and described for attachment to the ear, to an appendage, and/or to another region of the human body. However, it is to be understood that embodiments of the present invention are not limited to those worn by humans.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.; noise pollution experienced by the ear; and lighting conditions for the eye. Moreover, the region of the inner-ear between the anti-tragus and concha provides access to a rich vascular network for PPG-based monitoring and is relatively more consistent in size and shape across a broad population of humans, and vibrates less with motion (presents less motion artifacts) than other ear regions during PPG-based monitoring. Furthermore, as the ear canal is naturally designed for transmitting acoustical energy, the ear provides a good location for monitoring internal sounds, such as heartbeat, breathing rate, and mouth motion.

Optical coupling into the blood vessels of the ear, limbs, skin, or other portions of the body may vary between individuals. As used herein, the term "coupling" refers to the interaction or communication between excitation energy (such as light) entering a region and the region itself. For example, one form of optical coupling may be the interaction between excitation light generated from within a light-guiding earbud to the skin and then on to the blood vessels of the body. In one embodiment, this interaction may involve excitation light entering the body and scattering from blood or a blood vessel such that the temporal change in intensity of scattered light is proportional to a temporal change in blood flow within the blood vessel. In the case where a PPG sensor is integrated into a wearable device, such as an audio earbud, another form of optical coupling may be the interaction between excitation light generated by an optical emitter within the wearable device (in the case an earbud) and the light-guiding region of the wearable device.

Thus, a wearable device with integrated light-guiding capabilities, wherein light can be guided to multiple and/or select regions along the wearable device, can assure that each individual wearing the device will generate an optical signal related to blood flow through the blood vessels.

Optical coupling of light to a particular region of one person may not yield useable photoplethysmographic signals for each person. Therefore, coupling light to multiple regions may assure that at least one blood-vessel-rich region will be interrogated for each person wearing the light-guiding wearable device. Coupling multiple regions of the ear to light may also be accomplished by diffusing light from a light source within the earbud. Moreover, guiding light to multiple regions of the body (such as guiding light via a PPG sensor to multiple regions of the skin) may help generate scattered light signals from each region that, when averaged together, effectively average-out noise signals and effectively amplify blood flow signals. This effect may occur because whereas motion- or environmental-artifacts may be slightly different in each region, the blood flow signal may be similar in each region. Thus, averaging a plurality of signals, each from one of the plurality of body regions, may help increase the signal-to-noise ration of the desired blood flow signal.

Referring now to FIGS. 3-8, a sensor module 20, according to some embodiments of the present invention, will be described. The illustrated sensor module 20 includes a housing 30 and a sensor assembly 40 disposed within the housing 30. Though the sensor module 20 and associated housing 30 are shown as rounded or circular in FIG. 3, the sensor module 20 may have any shape suitable for supporting the components, such as triangular, polygonal, rectangular, etc., e.g., as shown in FIGS. 14A-14B, 15A-15B, 16A-16B.

The size of the sensor module 20 may be determined in part by the location of the body where the sensor module 20 is positioned. For example, a smaller sensor module 20 may be better suited for the ear or along a muscle group, whereas a larger sensor module 20 may be better suited for a flat surface, such as the wrist or forearm. However, ideally the sensor module is small enough to not "rock" on multiple muscle groups as they independently flex. For the case where the emitter and detector are both optical, the spacing between the emitter and detector is generally be between about 100 µm and 10 mm, such that the optical path affords substantial interaction between light from the emitter and blood flow scatter while also being short enough to prevent total optical absorption before returning to the detector.

The illustrated housing 30 includes first and second portions 32, 34 that are secured together via fasteners 36a, 36b. In the illustrated embodiment, fastener 36a is a screw or other threaded member that is inserted through the housing first portion 32 and threadingly engages a threaded insert 36b secured to the housing second portion 34. However, embodiments of the present invention are not limited to the use of threaded fasteners. Various ways may be utilized to secure the housing first and second portions 32, 34 together, as would be understood by one skilled in the art, such as molded connectors, screwing together the first and second portions 32, 34 without fasteners, clipping members, locking members, glue, welding, and the like. The purpose of having first and second portions 32, 34 is not for functionality but rather for ease of manufacturing, and so it should be understood that the sensor modules components may still function without a distinct first or second housing portion 32, 34, as long as at least one housing can support the sensor assembly. In some embodiments, one or both of the housing first and second portions 32, 34 are formed of substantially opaque material.

In some embodiments, the housing 30 is configured to removably receive a fastener (a fastening mechanism) for securing the sensor module 20 to a wearable article, such as an earbud, an armband, a wristband, a legband, a neckband, a ring, jewelry, glasses, headgear, a helmet, a safety strap, a patch, a tattoo, an earring, an article of clothing, etc. In other embodiments, the housing 30 may include a first magnet that is configured to removably secure the sensor module to a wearable article via a second magnet.

Figure 22:
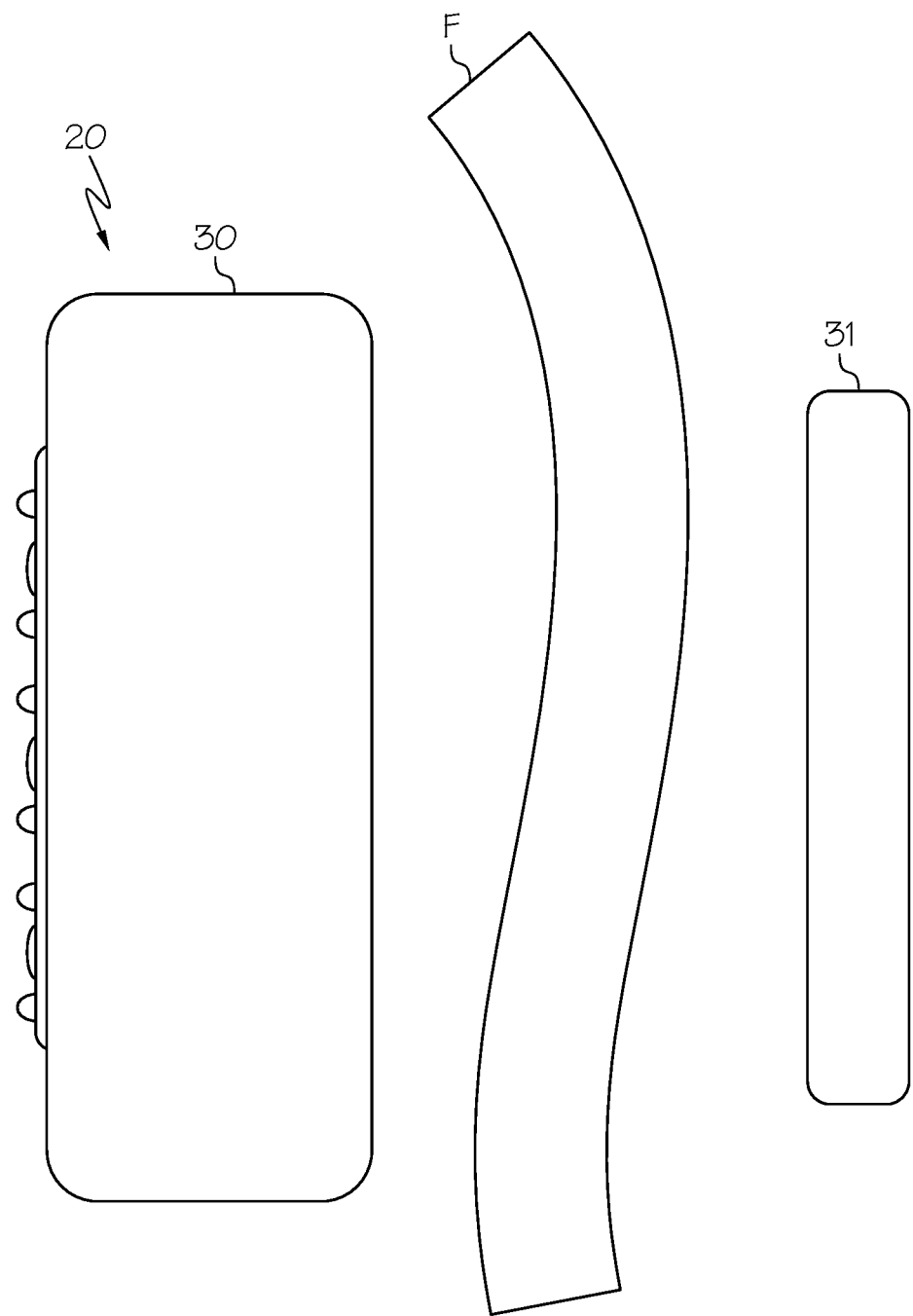
FIG. 22 is an exploded view of a wearable apparatus having the sensor module of FIG. 3, according to some embodiments of the present invention.

FIG. 22 illustrates the sensor module 20 being secured to a wearable article such as a fabric F via a fastener 31. Fastener 31 is depicted as a magnet in FIG. 22. As such, the housing 30 of the sensor module 20 includes a magnet (not shown) that is adapted to attract the magnet 31. However, embodiments of the present invention are not limited to the use of magnetic fasteners. Various ways may be utilized to secure sensor module 20 to a wearable article. A pin or clip may alternatively be used, for example. Other types of fasteners may be utilized also, such as hook and loop fasteners, etc.

Figure 23:
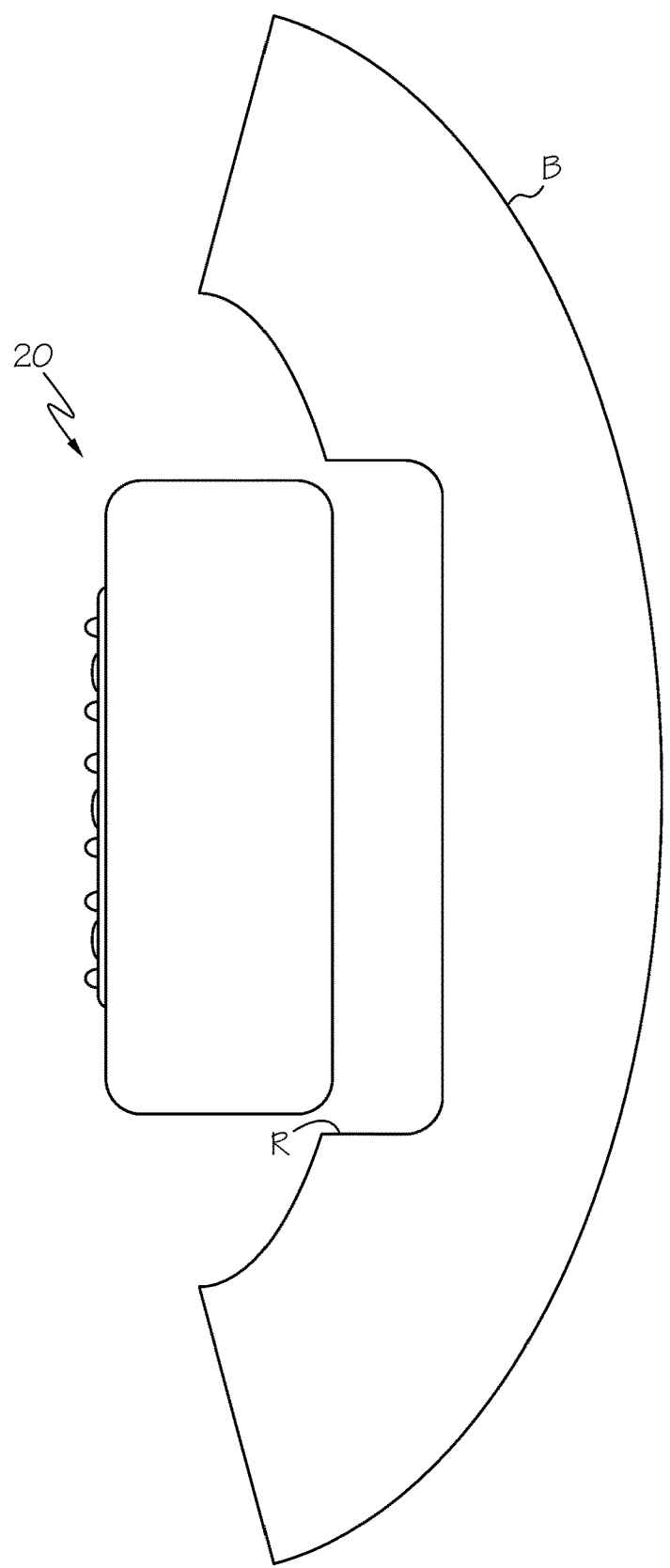
FIG. 23 is an exploded view of a wearable apparatus having the sensor module of FIG. 3, according to some embodiments of the present invention.

FIG. 23 illustrates the sensor module 20 being secured to a wearable article such as a wearable band B via a receptacle R formed within the band B and configured to retain the sensor module 20 therein. The sensor module 20 and receptacle R may further include a mated connector pair (not shown for simplicity), such as that illustrated in FIGS. 17A-17C.

Referring back to FIGS. 3-4, the sensor assembly 40 includes a base 42, such as a printed circuit board (PCB), that supports at least one optical emitter 44 and at least one optical detector 46. However, other types of energy emitters and detectors may be utilized in other embodiments of the present invention. For example, energy emitters that may be utilized in accordance with embodiments of the present invention may be configured to direct electromagnetic radiation, mechanical energy, acoustical energy, electrical energy, and/or thermal energy at the target region, and detectors may be configured to detect electromagnetic radiation, mechanical energy, acoustical energy, electrical energy, and/or thermal energy.

In the illustrated embodiment, the base 42 includes a plurality of optical emitters 44 and an optical detector 46. The optical emitters 44 are configured to direct optical energy at a target region of a portion of the body of a subject (e.g., a region of the ear, region of an appendage, wrist, finger, toe, torso, neck, etc.). The optical detector 46 is configured to detect an optical energy response signal from the target region and/or a region adjacent the target region.

Figure 4:
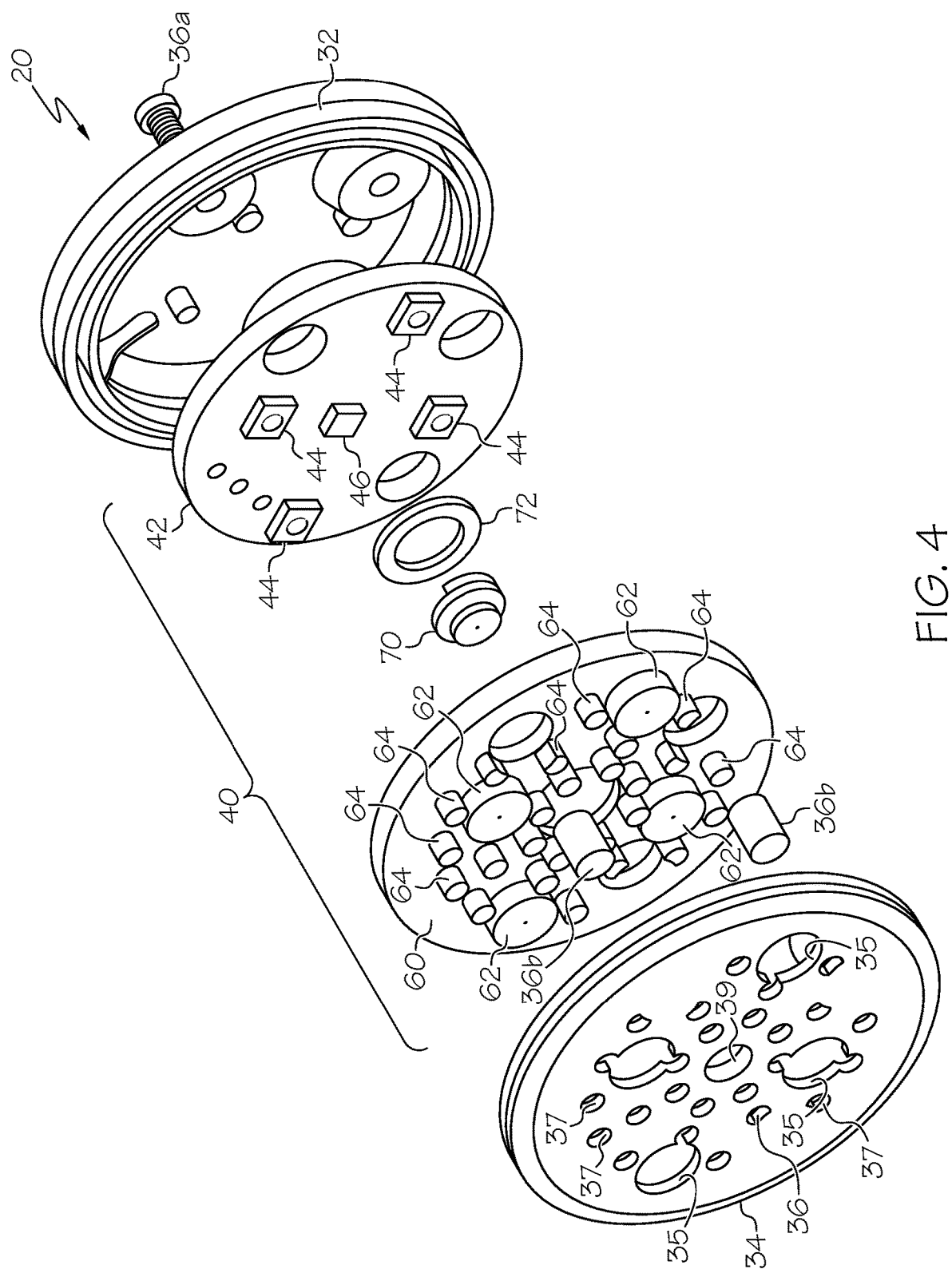
FIG. 4 is an exploded view of the sensor module of FIG. 3.
Figure 5:
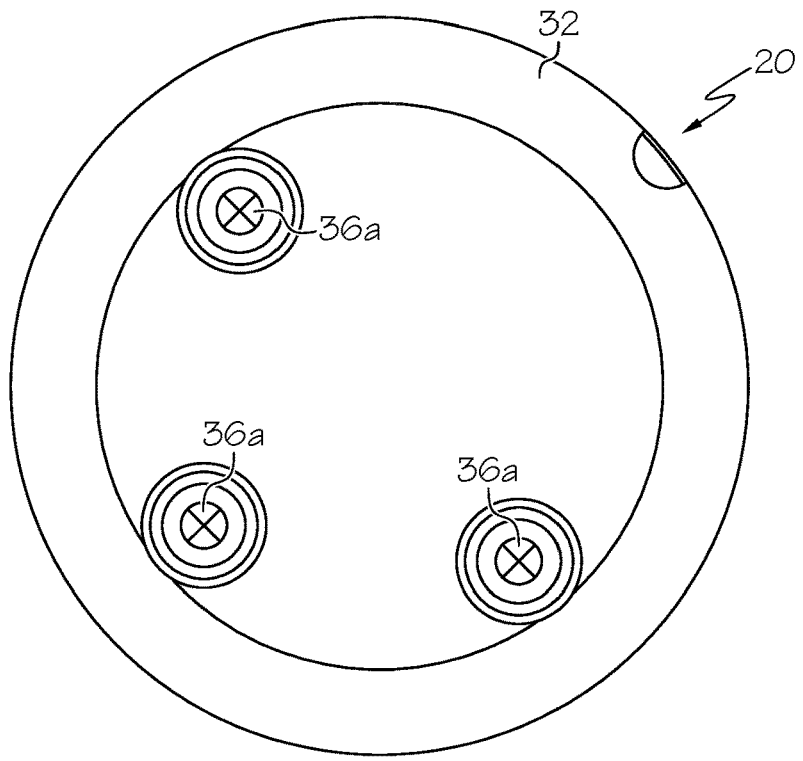
FIG. 5 is a top plan view of the sensor module of FIG. 3.

Though a plurality of optical emitters are shown in FIG. 4, in some embodiments, only one emitter may be used. Similarly, though only one optical detector 46 is presented in FIG. 4, a plurality of optical detectors may be employed. The use of a plurality of emitters and/or detectors can help with signal processing, as multiple individual signals can be averaged and or subtracted from different locations along the skin, providing an extracted signal that is "cleaner" (more representative of biometric information and less representative of other information, such as motion artifacts, environmental artifacts, and the like) than that which would be derived from a single detector alone. The provision of cleaner extracted signals is discussed in U.S. Pat. No. 8,251,903, which is incorporated herein by reference in its entirety.

Additionally, for the use of a plurality of detectors, each detector may be configured to detect a certain frequency range of energy, enabling the ability to process each detector signal individually based on the frequency response. For example, if the detectors are optical detectors, each optical detector may comprise an optical filter, such as (but not limited to) a separate optical filter placed on each detector or integrated optical filtering based on material properties of the optical sensor element, such that each detector is configured to primarily sense a different range of optical wavelengths. Similarly, a plurality of piezoelectric detectors (such as piezoelectric resonators), acoustic detectors, or ultrasonic detectors may be employed along the sensor assembly, with each detector tuned to a specific band of frequencies.

For the use of a plurality of emitters, each emitter may be configured to emit at a specific frequency band. For example, piezoelectric, acoustic, or ultrasonic emitters may be configured to generate frequencies within a certain band (or bands) of frequencies. Such tuning of frequency bands can be achieved by engineering the size of the emitters (such as piezoelectric actuators, acoustic speakers, or ultrasonic resonators) for a particular frequency band (or bands). If the emitter is an optical emitter, the emitter may be configured to generate optical wavelengths within a certain band of frequencies, affording analysis such as pulse oximetry ($SpO_2$) monitoring or skin or blood analyte monitoring, using methods understood by those skilled in the art.

Controlling the optical wavelength bands can be achieved by choosing a specific optical emitting element that has been configured to generate specified wavelengths of light. Alternatively or additionally, a specific example of controlling the wavelength bands in optical emitters according to some embodiments of the present invention comprises placing at least one optical filter between an emitting element and the region to be detected, such as depositing an optical filter on an optical emitting element or depositing or integrating an optical filter in the lensing, windows, or light-guiding material of the optical emitting region. A plurality of optical filters for wearable devices are known to those skilled in the art, and non-limiting embodiments are described in U.S. Pat. Nos. 8,320,982, 8,647,270, 8,700,111, and 8,888,701, which are incorporated herein by reference in their entireties.

Exemplary optical detectors 46 include, but are not limited to photodiodes, photodetectors, phototransistors, thyristors, solid state devices, optical chipsets, whether analog or digital, or the like. Many types of compact optical detectors exist in the marketplace today and comprise various well-known methods of generating analog or digital outputs. Exemplary optical emitters 44 include, but are not limited to light-emitting diodes (LEDs), laser diodes (LDs), compact incandescent bulbs, micro-plasma emitters, IR blackbody sources, or the like. In particular, optical chipsets are often "smart chips" that digitize the analog optical signal directly and many even provide some additional signal processing functions such as filtering or noise removal.

Figure 9:
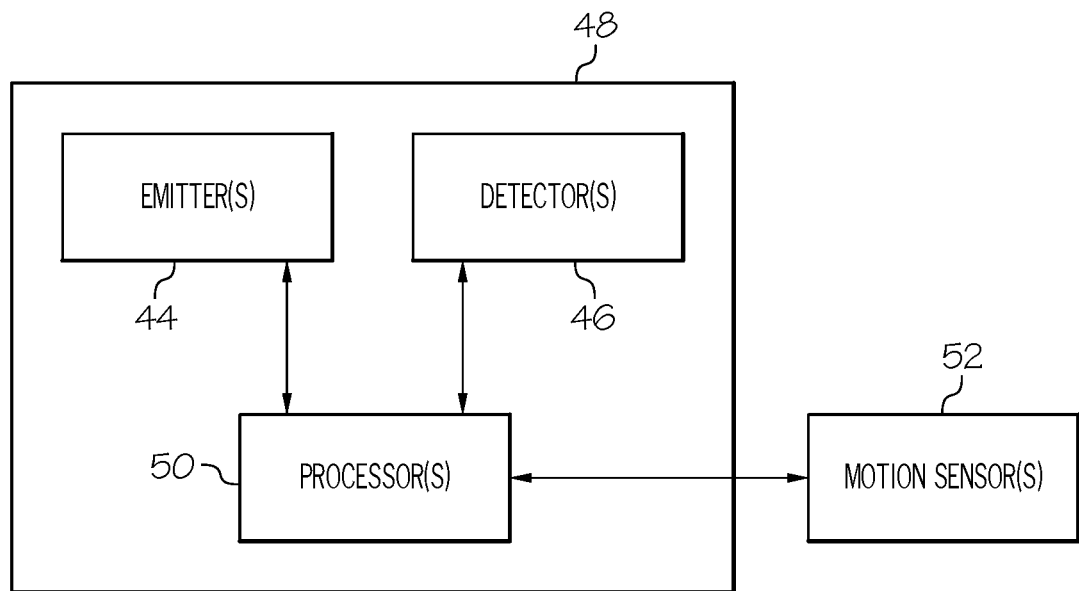
FIG. 9 schematically illustrates various electronic components that may be utilized in the sensor module of FIG. 3, according to some embodiments of the present invention.

The base 42 may include various other components, circuitry, etc. For example, in some embodiments as illustrated in FIG. 9, the sensor assembly 40 may include emitter(s) 44 and detector(s) 46, or emitter-detector modules 48, and one or more processors 50 for signal conditioning, A/D conversion, voltage-to-frequency conversion, level translation, and general signal processing of signals from the detector(s) 46. In some embodiments the sensor assembly 40 may include a motion sensor.

Additionally, one or more processors 50 may be used to control the powering (electrical biasing) of the emitter(s) 44 and/or detector(s) 46. A few examples are provided in U.S. Patent Application Publication No. 2012/0197093, which is incorporated herein by reference in its entirety. In some embodiments, the processor 50 may not be located on the base 42 and may even be located outside of the sensor module 20 altogether, as long as the processor 50 is in electrical communication (i.e., wired or wireless communication) with the emitter(s) 44 and/or detector(s) 46. Moreover, processor 50 may represent multiple processors distributed within the sensor module 20 and/or outside of the sensor module 20. For example, processing may be achieved by combining processing resources via a processor inside the sensor module 20 working in concert with a processor outside the sensor module 20 (such as a processor in a remote device or "the cloud").

The energy may be continuous or pulsed energy generated by an energy emitter 44. For example, a pulsed driving circuit (not shown) may be used to drive at least one energy emitter 44 at one or more pulsed frequencies to interrogate a target region with pulsed energy. An energy response caused by this interaction is detected by at least one detector 46, which is configured to detect energy in the forms described above. U.S. Pat. No. 8,888,701 describes non-limiting examples of suitable pulsing methods for the case where the sensor module 20 comprises optical emitters and optical detectors.

In some embodiments, the sensor module 20 may include a motion/position sensor 52 (e.g., an inertial sensor, MEMS (micro-electromechanical systems) sensor, accelerometer, gyroscope, capacitive sensor, inductive sensor, acoustic sensor, optical sensor, pressure sensor, piezoelectric sensor, etc.). The motion/position sensor 52 may be located on the base 42 and may be configured to sense or measure movement, positional changes, or inertial changes in the vicinity of the target region, such as gross body motion, skin motion, or the like. In some embodiments, the motion/position sensor 52 may comprise at least one pressure sensor configured to pick up pressure readings or changes between the sensor module 20 and the body of the person wearing the module 20.

The motion/position sensor 52 may also serve as a noise reference by a neighboring or remote processor (such as processor 50) for attenuating or removing motion noise from physiological signals picked up by the detector(s) 46. Noise attenuation and removal is described in detail in U.S. Pat. Nos. 8,157,730, 8,251,903, U.S. Patent Application Publication No. 2008/0146890, U.S. Patent Application Publication No. 2010/0217098, U.S. Patent Application Publication No. 2010/0217102, U.S. Provisional Patent Application No. 61/750,490, PCT Application No. US2012/071593, PCT Application No. US2012/071594, and PCT Application No. US2012/048079, which are incorporated herein by reference in their entireties.

The base 42 of the sensor module 20 may include other components such as one or more analog-to-digital convertors (not shown) for the output of the at least one detector 46, one or more filters such as optical filters (not shown) for removing the effects of time-varying environmental interference, one or more analog and/or digital filters for removing motion artifacts in an energy response signal, passive electronic components, etc., as would be understood by one skilled in the art. The base 42 of the sensor module 20 may include various other devices, such as other types of physiological sensors and environmental sensors (not shown). The base 42 of the sensor module 20 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 20 and may be charged via a USB charge port, for example.

The base 42 may be comprised of multiple portions which may be connected or separate. For example, the base 42 may have a first portion that supports one or more optical emitters 44 and a second portion that is separate from the first portion that supports the optical detector 46. The base 42 may include other portions that support various other electrical components, as well.

Thus, the sensor module 20 may be in wired or wireless communication with a remote device, such as a smartphone, computer, smart tablet, another sensor module, or other electronic devices. In some embodiments, the sensor module 20 may comprise a wireless powering mechanism, such as an inductive, optical, RF (radio frequency), or ultrasonic powering mechanism, such that electromagnetic induction, photovoltaic activity, RF energy harvesting, or ultrasonic actuation may be utilized to power the sensor module 20 independently of a localized battery. Various energy harvesting circuits for harvesting inductive, optical, RF, and ultrasonic energy may be utilized, and are well known to those skilled in the art. One advantage of wireless powering is that the sensor module 20 would not have to be separately charged if in communication with another wearable device that is powered by a battery and which comprises a wireless power transmitter, such as a magnetic inducting circuit, photon-generating circuit, RF antenna, or an ultrasonic transmission circuit. For example, if the sensor module 20 comprises a wireless powering mechanism, and if the module is integrated within an earpiece (such as shown in FIGS. 18A-18D, 19A-19B, and 20) comprising an earbud that is part of a headset, then the earbud sensor module 20 may be powered remotely by the battery-powered headset that comprises a wireless power transmitter. In such case, the sensor module 20 may never need to be separately charged from the headset circuitry, and the earbud sensor module 20 may be interchanged between headsets having similar wireless powering circuitry while the earbud sensor module 20 would, regardless of which headset it were in proximity with, maintain sensor functionality and wireless data transmission functionality for sending sensor data to a remote device.

The sensor assembly 40 also includes a guide layer 60 that overlies the base 42 in face-to-face relationship. The illustrated guide layer 60 includes a plurality of protrusions 62 extending outwardly to accommodate the plurality of energy emitters 44. In the illustrated embodiment, the protrusions have a cylindrical configuration (but may have other shapes as well, such as rectangular, spherical, etc.) and are in communication with the energy emitters 44. For example, in the embodiment where the energy emitters 44 are optical emitters, the protrusions 62 are in optical communication with the optical emitters 44. The light-guiding layer 60 and associated optical lenses and protrusions 62, comprising sufficiently optically transparent material having an index of refraction substantially greater than that of air, may serve as light guides directing light into the skin of a subject. In this case, the light-guiding layer 60 and associated optical lenses and the protrusions 62 may be comprised of plastic, polymer (such as polyurethane, rubber, polychloroprene, polyamides, polyesters, acrylics, silicone, polyethylene, polyphosphonates, polypropylene, poly(vinyl chloride), and polystyrene or the like), glass, epoxy, crystalline material, or an optically filtering material (such as materials comprising optical dyes, quantum dots, optical interference filters, or the like), etc.

The protrusions may comprise rigid or resilient material. The protrusion material is chosen to be both reasonably solid and also to be sufficiently optically transparent for the chosen emitter and/or detector optical wavelength range. In the case where the protrusion material is not sufficiently optically transparent, the material may be thinned at the tip of the protrusion region to pass at least some level of light. In some embodiments the protrusions are comprised of resilient material to help with gripping the protrusions along the skin of an individual.

The guide layer 60 also includes a plurality of outwardly extending stabilizing members 64. The protrusions 62 and stabilizing members 64 may be formed from resilient material, such as silicone, polymeric material, rubber, soft plastic, other elastomeric materials, or other compressible materials. However hard materials such as acrylic, hard plastic, hard polymeric material, glass, polycarbonate, metal, and the like may also be used. Various shapes, configurations, and materials may be utilized to implement the protrusions 62 and stabilizing members 64, without limitation. In some embodiments, the protrusions 62 and stabilizing members 64 may have a durometer range from about 10 (Type OO—ASTM D2240) to 80 (Type A—ASTM D2240), and a hardness range of about 20-50 Shore A, for example.

Unlike the protrusions 62, a primary purpose of the stabilizing members 64 is not to guide energy (i.e., optical energy) between the emitter 44 or detector 46 and the skin of the user, but rather to provide mechanical stabilization. The stabilizing members 64 are configured to engage the skin of a subject wearing the sensor module 20. The stabilizing members 64 are configured and spaced apart to stabilize the sensor module 20 relative to the skin of a subject such that the protrusions 62 in communication with the emitters 44 and detector 46 remain in place in proximity to (or against) the skin of a subject. Moreover, the stabilizing members 64 may be formed from hard or resilient material and have a configuration and spacing that stabilizes against the skin of the subject without pushing away blood in the skin region of contact. It should be noted that an added benefit of resilient material may be that the material may be more comfortable to wear than a hard material. In addition to positional stabilization, the shock absorbing characteristics of the stabilizing members 64 when formed from elastomeric material or other resilient material may help reduce energy pathway (e.g., an optical pathway from an optical emitter and/or to an optical detector, etc.) deformation in the skin/body of the subject such that an energy pathway may not change as abruptly as a result of motion of a subject wearing the sensor module 20.

Figure 6:
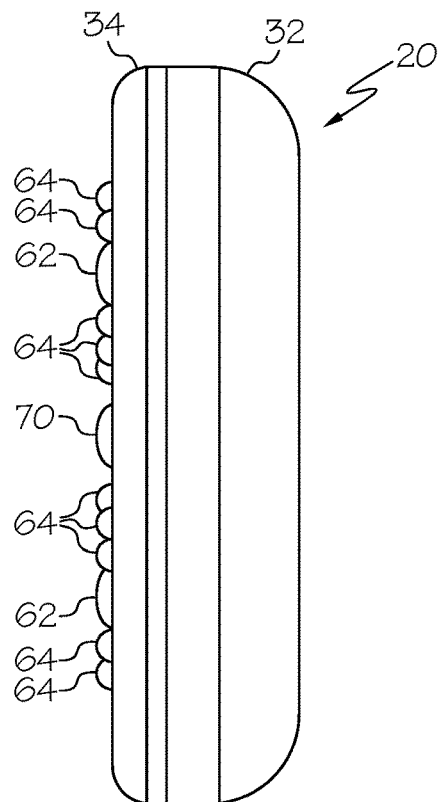
FIG. 6 is a side view of the sensor module of FIG. 3.

The housing second portion 34 includes a plurality of first openings 35 through which the respective protrusions 62 extend, and a plurality of second openings 37 through which the stabilizing members 64 extend. As illustrated in FIG. 6, the stabilizing members 64 and protrusions 62 extend through the housing second portion 34 and are configured to contact the skin of a subject wearing the sensor module 20 (i.e., wearing a device incorporating the sensor module 20). In some embodiments of the present invention, one or more of the stabilizing members 64 have an outwardly extending length that is greater than an outwardly extending length of the protrusions 62.

As described earlier, in some embodiments, the first and second housing portions 32, 34 may be integrated together, and need not be physically separable components. Moreover, it should be noted that all or part of the stabilizing members 64 and/or protrusions 62 may be integrated within the housing 30 of the sensor module 20. Such a configuration may be achieved by co-molding the housing 30, stabilizing members 64 and/or protrusions 62, for example. As such, in some embodiments, the guide layer 60 is not required since the stabilizing members 64 and/or protrusions 62 may be integrated within the housing 30.

In the illustrated embodiment, energy emitters 44 are optical emitters and the energy detector 46 is an optical detector. The sensor module 20 includes a lens 70 that overlies and that is in optical communication with the optical detector 46. The illustrated sensor module 20 also includes an optical isolation gasket 72 that is configured to be a blocking region and thus isolate the optical detector 46 from direct light emitted by the optical emitters 44. The guide layer 60 includes an opening 61 that is configured to accommodate the lens 70. The housing second portion 34 includes a third opening 39 through which the lens 70 extends.

In other embodiments, the guide layer 60 may include a protrusion extending outwardly therefrom to accommodate the energy detector 46 in lieu of the opening 61.

In some embodiments, the sensor module 20 may include a coupler (not shown) that is associated with at least one energy emitter 44 and/or with the energy detector 46. For embodiments of the present invention using optical energy emitters and detectors, the coupler may comprise a lens or other light guiding feature. As a specific example, the lens 70 illustrated in FIG. 4 is an example of an optical coupler. For embodiments of the present invention using electrical energy emitters and detectors, the coupler may comprise an electrode or other electrically conductive feature. For embodiments of the present invention using thermal energy emitters and detectors, the coupler may comprise a thermally conductive material. For embodiments of the present invention using mechanical energy emitters and detectors, the coupler may comprise a mechanical actuator (such as a piezoelectric actuator, a motor, a vibrator, or the like) for the emitter and a mechanical transducer (such as a piezoelectric sensor, a photomechanical sensor, a thermomechanical sensor, or the like) for the detector. For embodiments of the present invention using mechanical energy emitters and detectors, a coupler may comprise a rigid material to help couple mechanical energy to/from a subject wearing the module 20. Such couplers may enhance and/or facilitate the transfer of energy from an emitter to the body of the subject and to a detector from the body of the subject.

Figure 7:
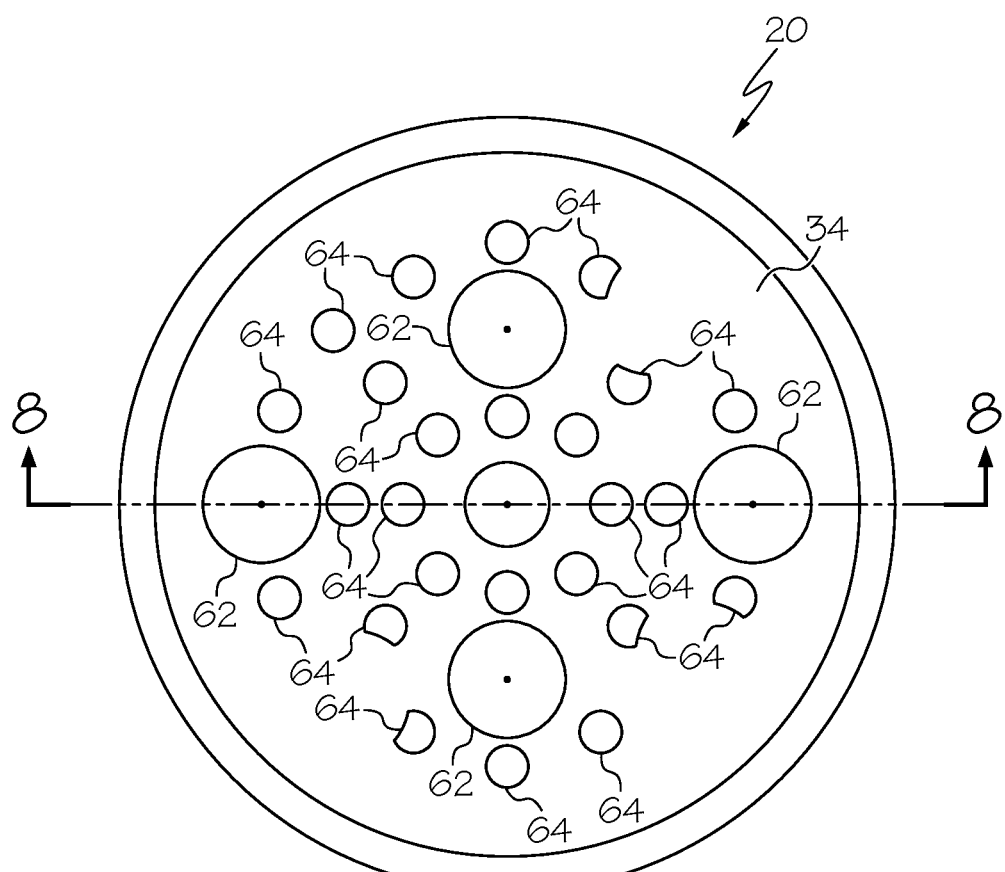
FIG. 7 is a bottom plan view of the sensor module of FIG. 3.
Figure 8:
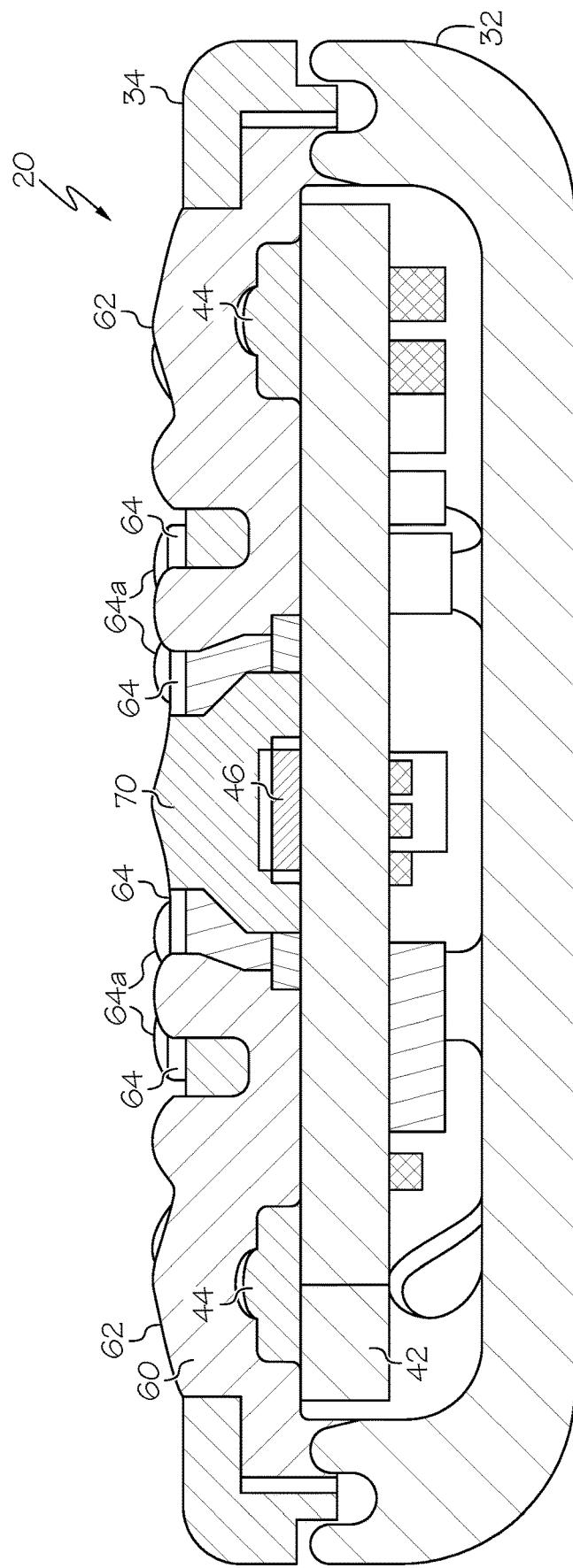
FIG. 8 is a cross-sectional view of the sensor module of FIG. 7 taken along line 8-8.

As illustrated in FIGS. 4 and 7, at least some of the stabilizing members 64 are substantially cylindrical and have a substantially circular cross-sectional profile, and at least some of the stabilizing members 64 are partially cylindrical and have a partially circular cross-sectional profile. However, the stabilizing members 64 may have various shapes and configurations.

In some embodiments, the stabilizing members 64 are arranged in a pattern. However, in other embodiments, the stabilizing members 64 may have a somewhat random arrangement. Typically, at least one stabilizing member 64 is located near each protrusion 62 to facilitate stabilization of the protrusion 62 relative to the skin of a subject wearing the sensor module 20.

Figure 11A:
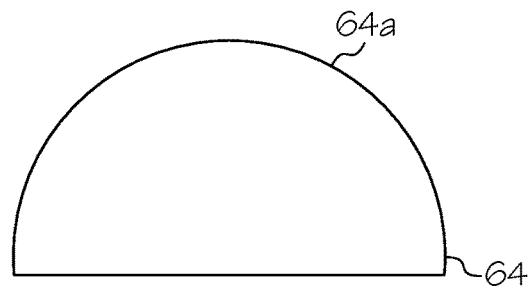
FIGS. 11A-11D illustrate various stabilizing member distal end configurations for the sensor module of FIG. 3, according to some embodiments of the present invention.
Figure 11B:
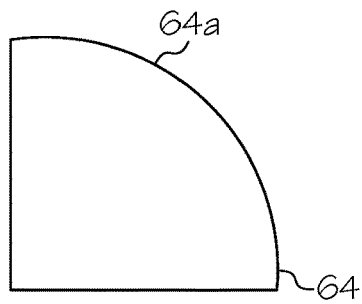
Figure 11C:
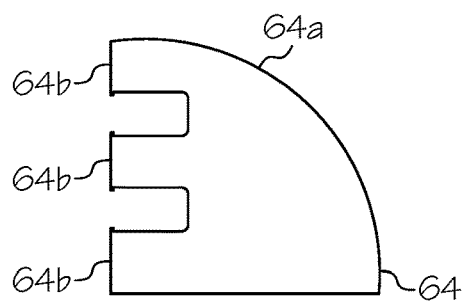
Figure 11D:
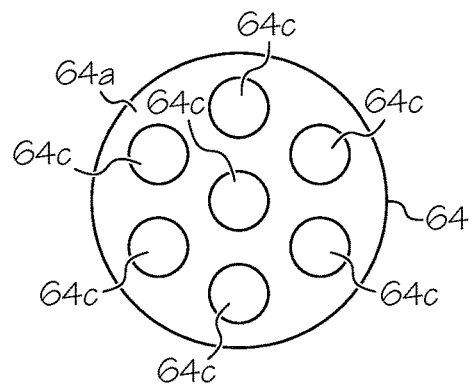

The distal ends 64a of the stabilizing members 64 may have various shapes and configurations, as illustrated in FIGS. 11A-11D. For example, in some embodiments, one or more of the stabilizing members 64 have a distal end 64a with a rounded configuration, as illustrated in FIG. 11A, or a partially rounded configuration, as illustrated in FIG. 11B. In some embodiments, one or more of the stabilizing members 64 have a distal end 64a with a plurality of teeth 64b, as illustrated in FIG. 11C. In some embodiments, one or more of the stabilizing members 64 have a distal end 64a with a textured configuration (e.g., a plurality of raised portions or bumps 64c, etc.) as illustrated in FIG. 11D. In some embodiments, the cross-section of the stabilizing members 64 that contact with the skin is more than about 0.5 mm and less than about 5 mm.

Figure 10:
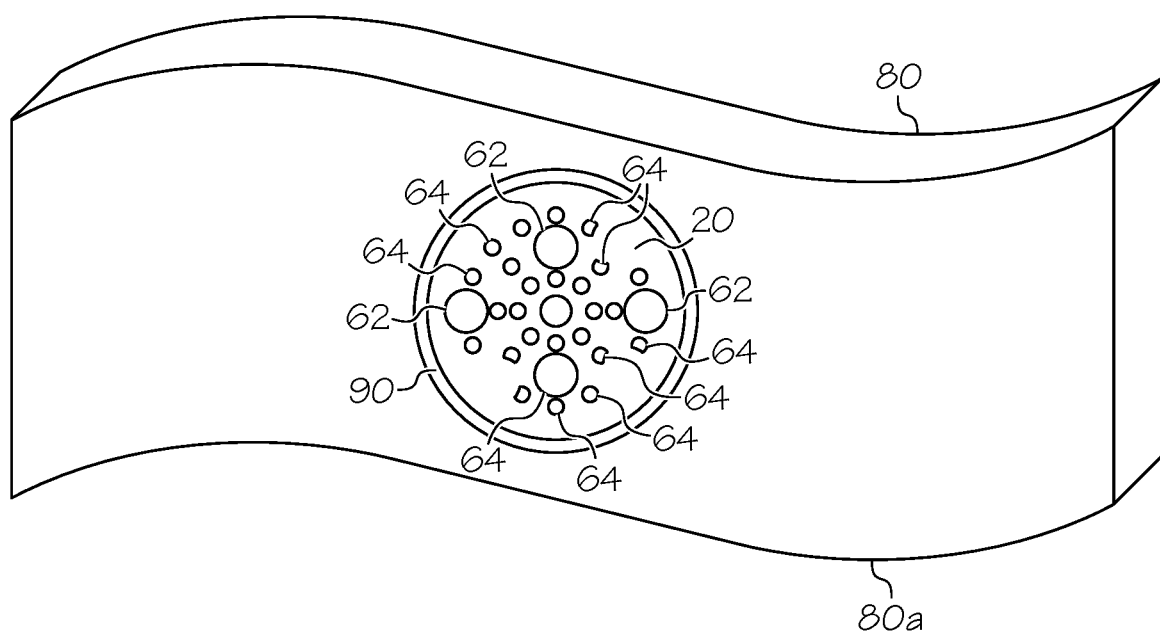
FIG. 10 illustrates a wearable band having the sensor module of FIG. 3 secured therewithin, according to some embodiments of the present invention.

FIG. 10 illustrates the sensor module 20 secured to a wearable band 80, according to some embodiments of the present invention. The illustrated band 80 may be configured to be secured to an appendage (such as a limb or digit, e.g., an arm, wrist, finger, toe, leg, neck, etc.) of a subject. Non-limiting configurations for keeping the band 80 on a limb or digit of a subject may include a molded continuous loop, a segmented loop, a clap or fastening mechanism (not shown), or the like.

Figure 24:
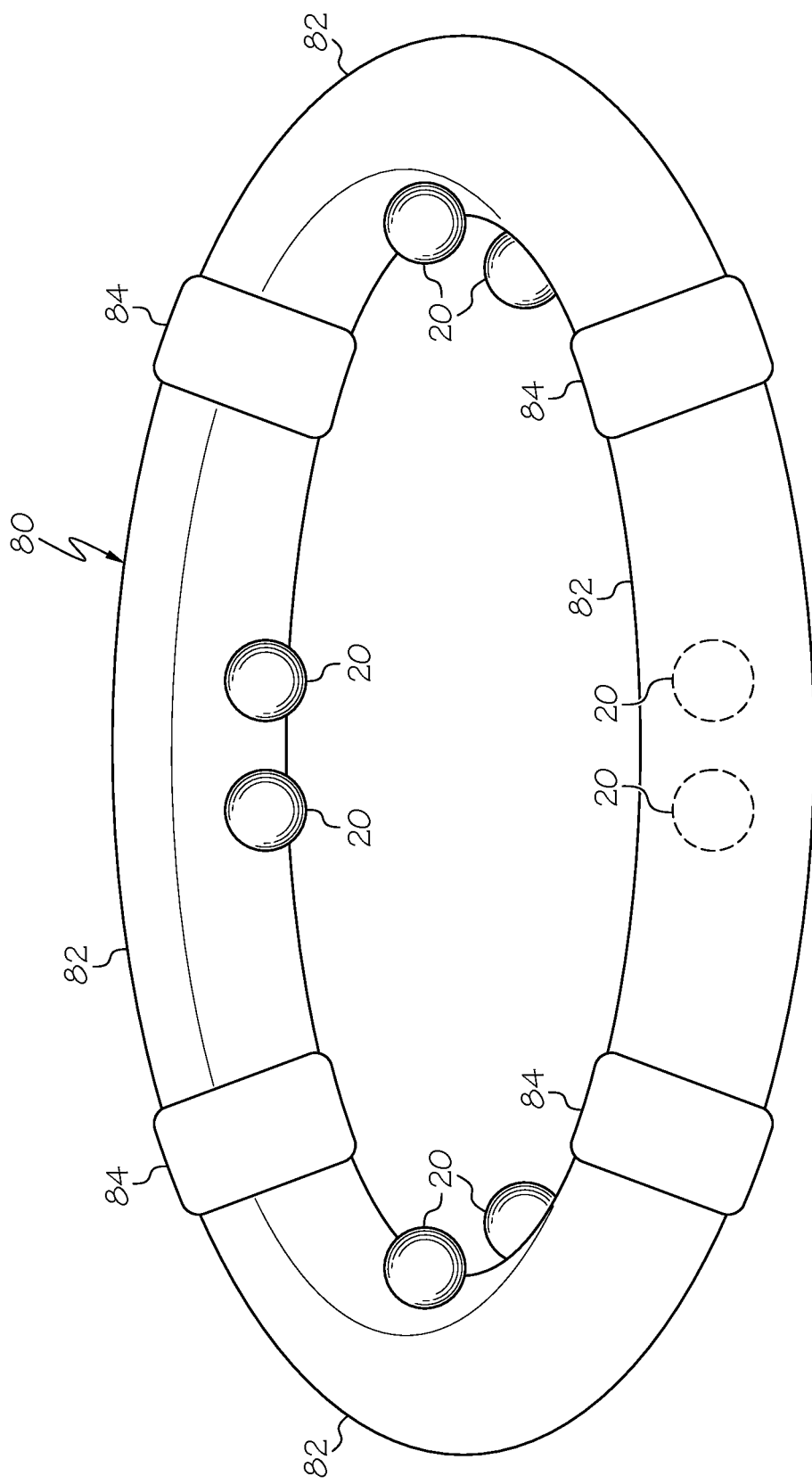
FIG. 24 is a perspective view of a wearable sensor band having one or more sensor modules such as the sensor module of FIG. 3, and having segments separated by mechanical stress-relieving components, according to some embodiments of the present invention.

In the embodiment of a wearable band 80 having a configuration of a segmented loop, illustrated in FIG. 24, the segments 82 of the band 80 may be connected by one or more mechanical stress-relieving components 84. A key function of a stress-relieving component 84 is that it can stretch and absorb mechanical energy without unhinging the band 80 to help prevent abrupt displacement of the sensor module(s) 20 from the skin during "fidgets" (sudden body motions), which can lead to errors in sensor detector readings. Non-limiting examples of stress-relieving components 84 include: molded material that has a lower durometer value than that of the material of the band 80, a spring, a flexible fabric or other flexible member, or the like.

Figure 25A:
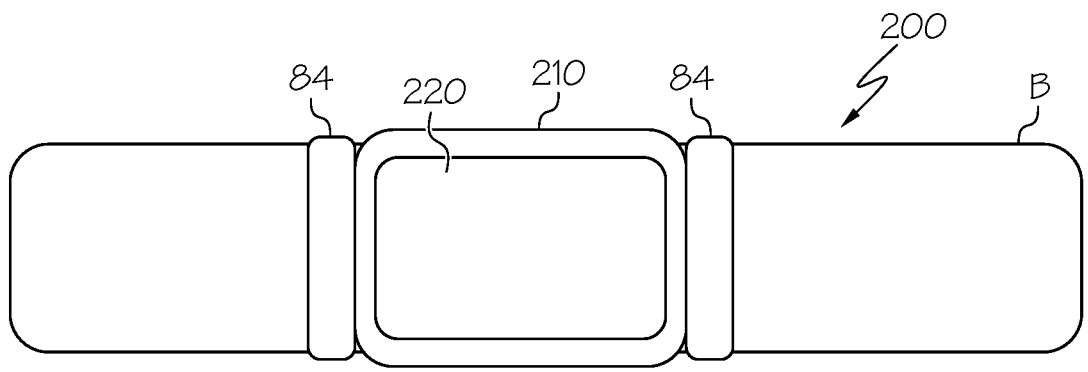
FIG. 25A is a top plan view of an exemplary wearable device having a sensor module, such as the sensor module of FIG. 3, disposed within a housing thereof, and having a band with stress-relieving components, according to some embodiments of the present invention.
Figure 25B:
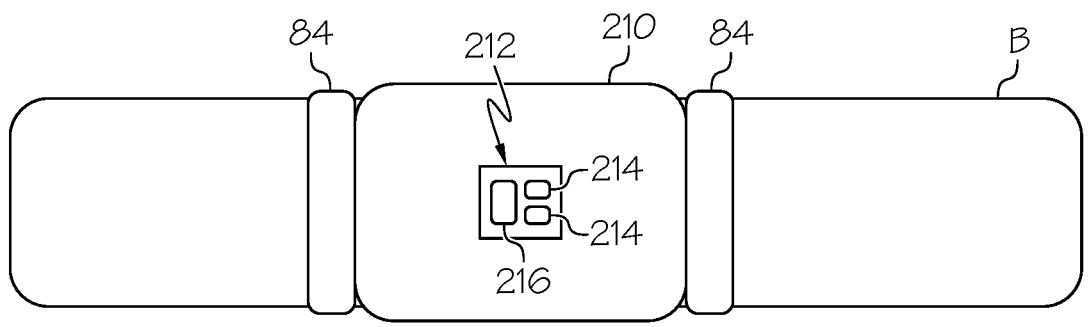
FIG. 25B is a bottom plan view of the device of FIG. 25A illustrating the sensor module.
Figure 25C:
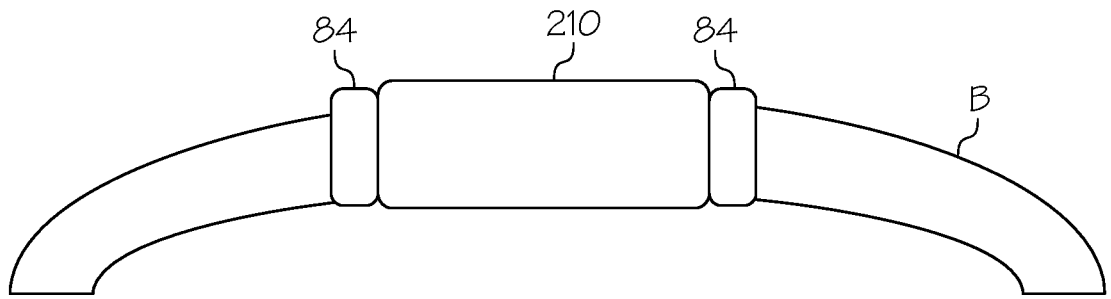
FIG. 25C is a side view of the device of FIG. 25A.
Figure 26:
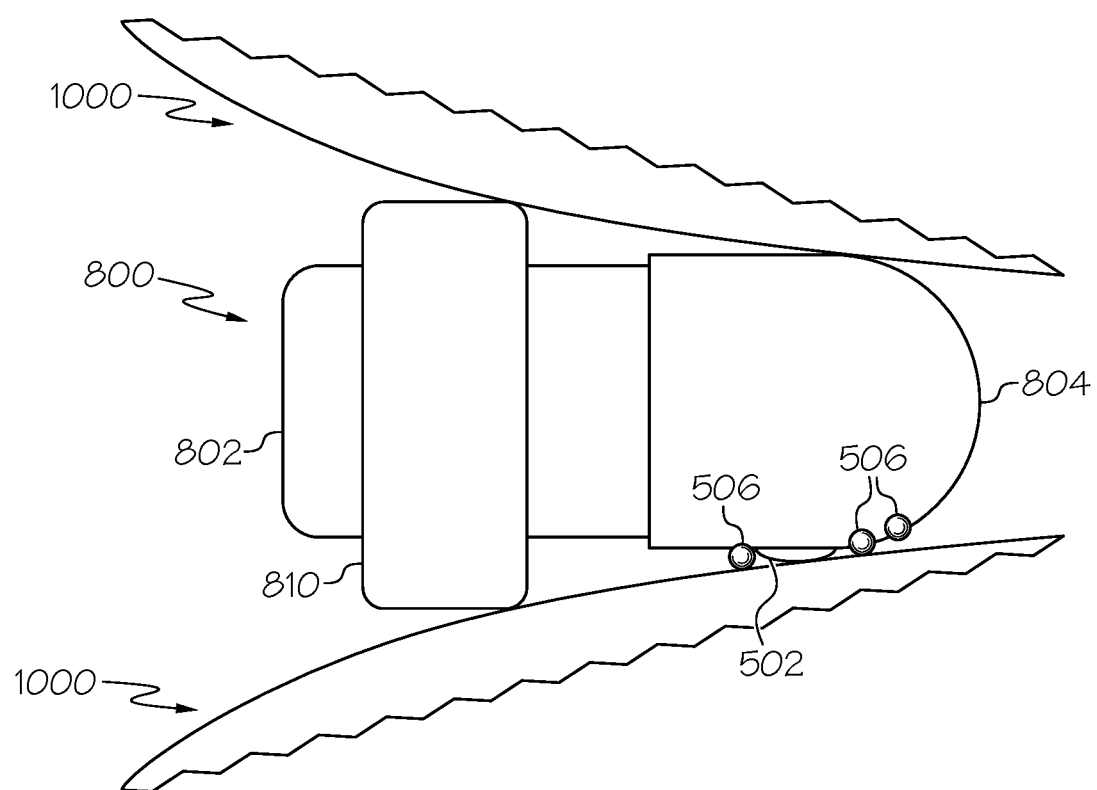
FIG. 26 is a side view of an in-ear sensing device positioned within an ear canal of a subject, according to some embodiments of the present invention.

Additional non-limiting examples of a wearable device having a band with stress-relieving components are illustrated in FIGS. 25A-25C. FIGS. 25A-25C illustrate a wearable monitoring device 200 that includes a housing 210 having a screen 220 attached to a band B that is configured to be secured around an appendage of a subject. The housing 210 includes a portion 210a with a biometric sensor 212 that is wearably positionable adjacent the skin of a subject. The biometric sensor 212 includes one or more optical emitters 214 and one or more optical detectors 216 (FIG. 25B). As illustrated in FIG. 25C, the biometric sensor 212 does not extend outwardly from the housing portion 210a. The band B includes a pair of stress-relieving components 84 that are configured to stretch and absorb mechanical energy to help prevent abrupt displacement of the sensor module 212 from the skin during "fidgets" (sudden body motions), which can lead to errors in sensor detector readings.

Referring back to FIG. 10, the illustrated band 80 includes an inner surface 80a in which the sensor module 20 is secured, and has a first Durometer value. The sensor module 20 is secured to the band 80 via supporting material 90 that has a second Durometer value that is lower than the first Durometer value. By having a lower Durometer value, the supporting material 90 acts as a suspension region for the sensor module that provides stability to the sensor module 20 when the band 80 is secured to a subject.

The configuration of FIG. 10 may also apply to a patch form-factor embodiment of the present invention. For example, an adhesive layer may be applied to the inner surface 80a of a band 80 for affixing the sensor module 20 to the skin. In such case, a circumferential band may not be required, as a rectangular (or other shape) adhesive patch form-factor is used.

Figure 12A:
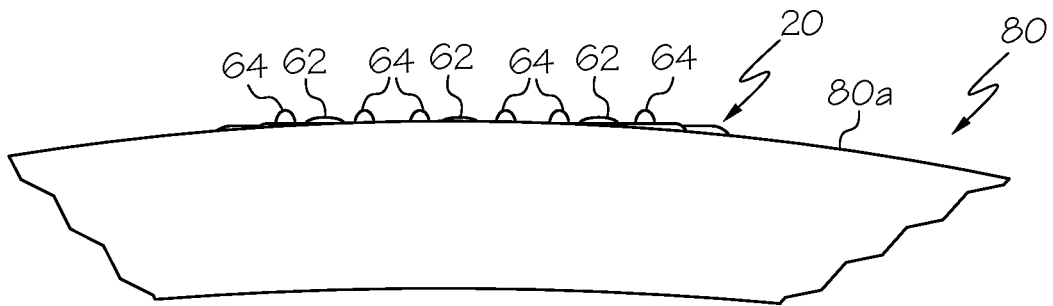
FIG. 12A is a side view of the wearable band and sensor module of FIG. 10.
Figure 12B:
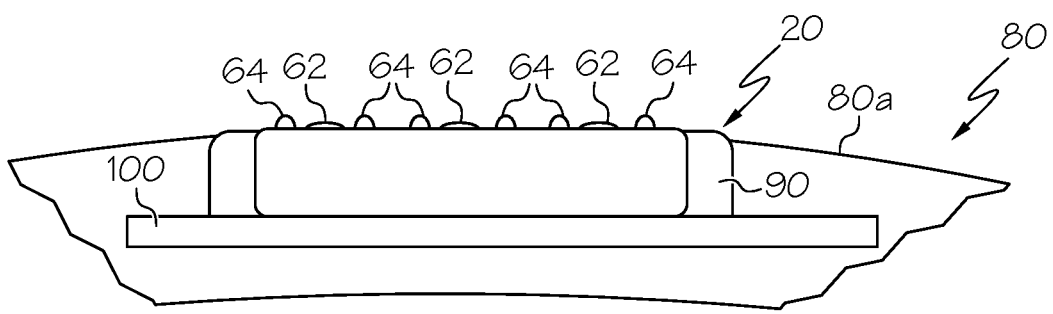
FIG. 12B is a cutaway side view of the wearable band and sensor module of FIG. 10 illustrating the configuration of supporting material around the sensor module, according to some embodiments of the present invention.
Figure 12C:
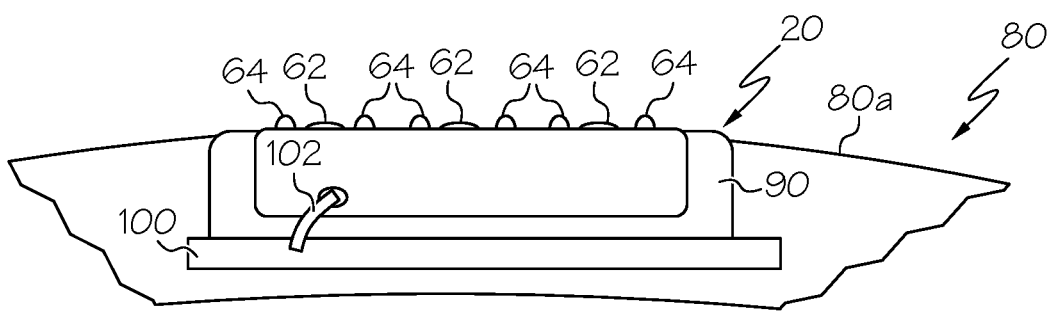
FIG. 12C is a cutaway side view of the wearable band and sensor module of FIG. 10 illustrating the configuration of supporting material around the sensor module, according to some embodiments of the present invention.

FIG. 12A is a side view of the wearable band 80 and sensor module 20 of FIG. 10. As illustrated, the sensor module is positioned within the band 80 such that the protrusions 62 and stabilizing members 64 extend outwardly from the inner surface 80a of the band 80. In some embodiments, the supporting material 90 extends substantially around a periphery of the sensor module 20, as illustrated in FIG. 12B. In other embodiments, the supporting material 90 extends substantially around a periphery and beneath the sensor module 20, as illustrated in FIG. 12C. A key benefit of having supporting material 90 beneath the sensor module 20 is that the supporting material 90 may help absorb mechanical energy in the vertical direction, whereas supporting material at the sides may help absorb sheer mechanical energy from the sides of the sensor module 20.

Also, as illustrated in FIGS. 12B-12C, the sensor module and supporting material is positioned on a base 100, such as a printed circuit board (PCB) or other substrate, and from which the sensor module may obtain power. FIG. 12C illustrates a wire or electrical connection 102 between the sensor module 20 and the base 100. As described above, wireless powering may alternatively or additionally be employed, such that the band electronics in the base 100 may wirelessly power the sensor module 20.

Referring now to FIGS. 21A-21D, a monitoring device 110, according to some embodiments of the present invention, is illustrated. The monitoring device 110 includes a housing 112 that is configured to be removably secured to a wearable article, such as an earbud, hearing aid or other earpiece, an armband, a wristband, a legband, a neckband, a ring, jewelry, glasses, headgear, a helmet, a safety strap, a patch, a tattoo, an earring, an article of clothing, etc. The housing 112 is formed from material having a first Durometer value.

A sensor module 20, as described above, is secured to the housing 112 via supporting material 114. The supporting material 114 has a second Durometer value that is lower than the first Durometer value. By having a lower Durometer value, the supporting material 114 acts as a suspension region for the sensor module 20 that provides stability to the sensor module 20 when the housing 112 is secured to a wearable article. In some embodiments, the supporting material 114 extends substantially around a periphery of the sensor module 20 (as illustrated in FIG. 12B). In other embodiments, the supporting material 114 substantially surrounds the sensor module 20 (as illustrated in FIG. 12C). The suspension region generally mechanically decouples the anchoring in the skin (via the stabilizing members 64) from the mounting support, band, fastener, or housing (i.e., earbud housing, armband housing, etc.).

The housing 112 may support various electronics for the sensor module 20, such as a power supply (e.g., a battery, etc.), power control, etc. In some embodiments, the housing 112 is configured to receive a fastener 116, such as a lapel pin, clip, etc., and is configured to be removably secured to a wearable article via the fastener. In other embodiments, the housing 112 includes comprises a first magnet (not shown) and is configured to be removably secured to a wearable article via a second magnet, which serves as fastener 116.

Figure 2A:
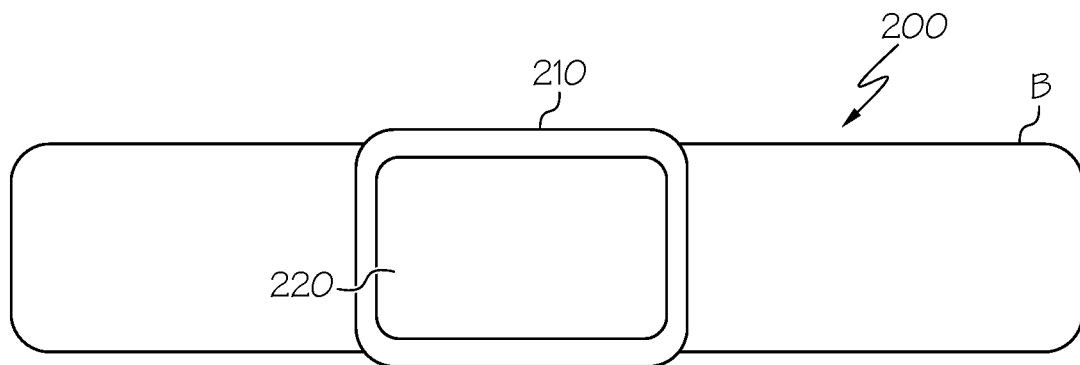
FIG. 2A is a top plan view of an exemplary wearable device having a sensor module disposed within a housing thereof for monitoring the heart rate of a person wearing the device.
Figure 2B:
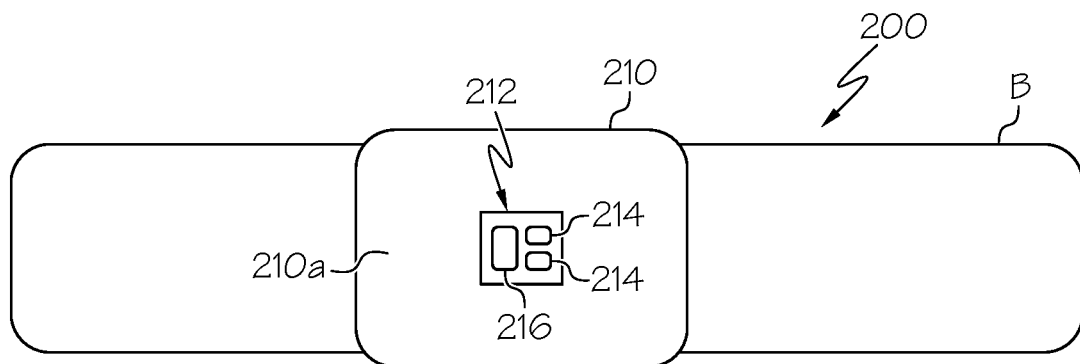
FIG. 2B is a bottom plan view of the device of FIG. 2A illustrating the sensor module.
Figure 2C:
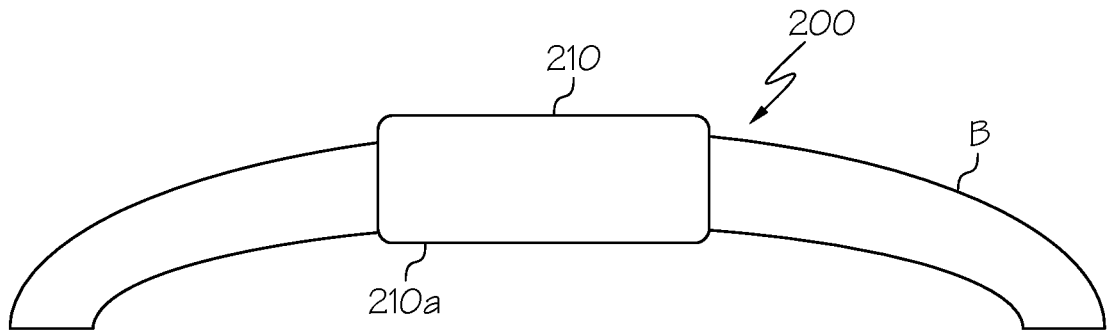
FIG. 2C is a side view of the device of FIG. 2A.
Figure 3:
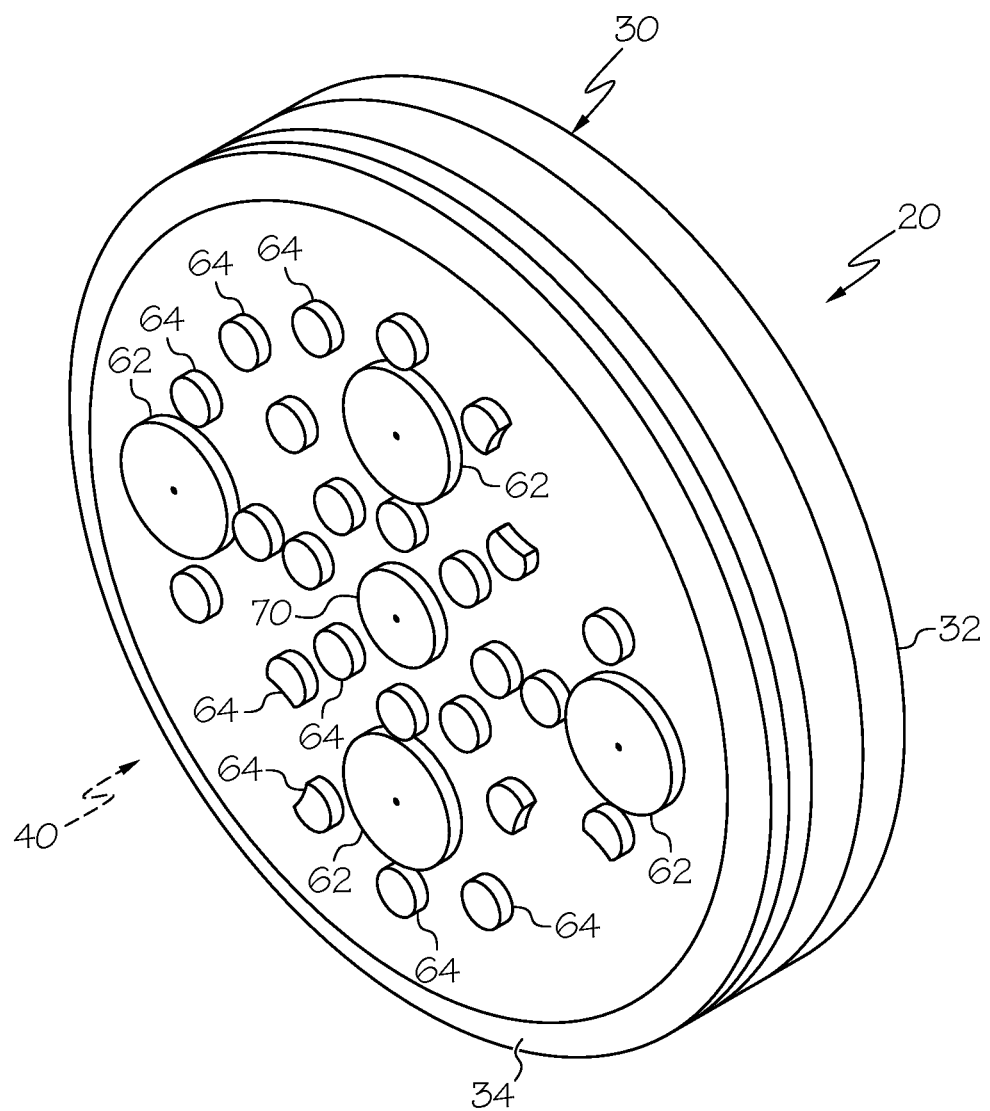
FIG. 3 is a perspective view of a sensor module that may be utilized in various wearable devices, according to some embodiments of the present invention.

Referring now to FIGS. 13A-13B, 14A-14B, 15A-15B, 16A-16B, and 17, optical adapters configured to be secured to conventional, third party wearable monitoring devices, such as the monitoring device 200 of FIGS. 2A-2C, are illustrated. The monitoring device 200 includes a housing 210 having a screen 220 attached to a band B that is configured to be secured around an appendage of a subject. The housing 210 includes a portion 210*a* with a biometric sensor 212 that is wearably positionable adjacent the skin of a subject. The biometric sensor 212 includes one or more optical emitters 214 and one or more optical detectors 216 (FIG. 2B). As illustrated in FIG. 2C, the biometric sensor 212 does not extend outwardly from the housing portion 210*a*. Biometric information from the sensor 212 (as well as other information) can be viewed via the screen 220.

Figure 13A:
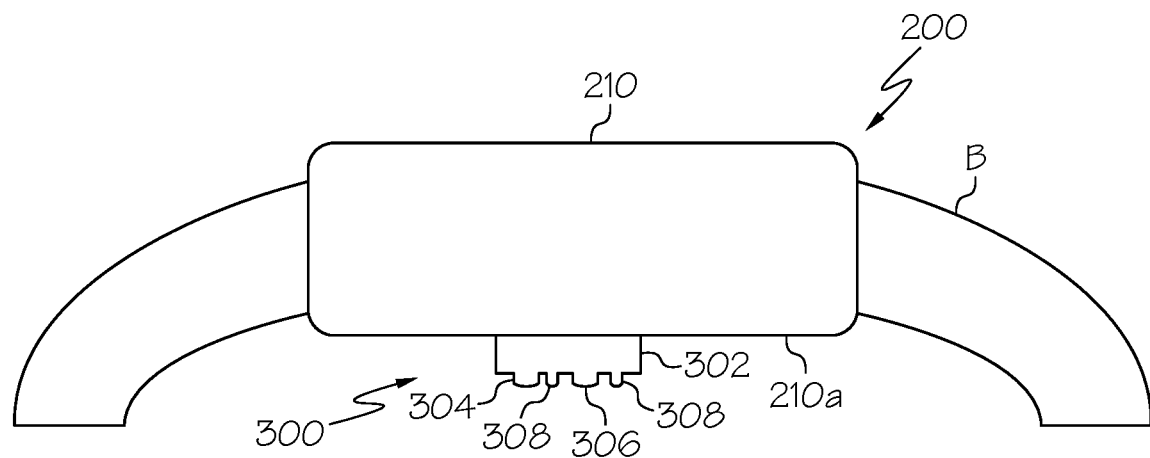
FIG. 13A illustrates an optical adapter secured to a wearable monitoring device having an optical sensor module, according to some embodiments of the present invention.

In FIG. 13A, an optical adapter 300, according to some embodiments is secured to the housing portion 210*a* of the monitoring device 200 of FIGS. 2A-2C. The adapter 300 includes a base 302 that is removably secured to the housing portion 210*a* of the monitoring device 200. First and second light guides 304, 306 extend outwardly from the base 302, and a plurality of stabilizing members 308 extend outwardly from the base 302. In some embodiments, the light guides 304 and 306 in effect may behave as the protrusions 62 described above with respect to FIGS. 3-8, and the stabilizing members 308 may behave as stabilizing members 64 described above with respect to FIGS. 3-8.

In some embodiments, the base 302 is adhesively secured to the housing portion 210*a*. For example, in some embodiments, one or more portions of the base 302 may be adhesively secured to the housing portion 210*a*. In other embodiments, the base 302 includes at least one male connector that is configured to engage at least one female connector associated with the housing portion 210*a*. In other embodiments, the base 302 includes at least one female connector configured to engage at least one male connector associated with the housing portion 210*a*. Other types of connecting mechanisms commonly known in the art may be used, such as sliding connectors, magnetic connectors, vacuum connectors, snap-in connectors, and the like.

The first light guide 304 is in optical communication with the optical emitter(s) 214 of the biometric sensor 212 (FIG. 2B) in the monitoring device 200 when the base 302 is secured to the housing portion 210*a*. The first light guide 304 has a free distal end that is configured to engage a portion of a body of the subject and to deliver light from the optical emitter(s) 214 directly into the body of the subject. The second light guide 306 is in optical communication with the optical detector 216 of the biometric sensor 212 (FIG. 2B) when the base 302 is secured to the housing portion 210*a*. The second light guide 306 has a distal end that is configured to engage a portion of the body of the subject. The second light guide 306 is configured to collect light directly from the body of the subject via the distal end thereof and deliver collected light to the optical detector 212. The first and second light guides 304, 306 are formed from elastomeric light transmissive material.

The light guides 304, 306 and stabilizing members 308 may be comprised of the materials described previously for the protrusions 62 and stabilizing members 64 of FIGS. 3-8. The stabilizing members 308 are formed from hard or resilient material and are configured to engage the skin of a subject wearing the monitoring device 200. In some embodiments, each stabilizing member 308 has an outwardly extending length from the base 302 that is greater than an outwardly extending length of the first and second light guides 304, 306 from the base 302. The stabilizing members 308 are configured to stabilize the biometric sensor 212 relative to the skin of a subject and provide better optical coupling between the first and second light guides 304, 306 and the optical emitter(s) 214 and detector 216. As described above, the stabilizing members 308 have a configuration and spacing that stabilizes the device around the skin region for energy interrogation (such as optical interrogation when the energy emitter is an optical emitter) without pushing away blood from the interrogation region (i.e., the skin region facing the energy emitter(s) and/or energy detector(s)).

In some embodiments, the base 302, first and second light guides 304, 306, and stabilizing members 308 are formed from the same or similar material, such as silicone, polycarbonate, glass, acrylic, or other sufficiently optically transparent material, as described above.

In some embodiments, at least some of the stabilizing members 308 are substantially cylindrical and have a substantially circular cross-sectional profile, and at least some of the stabilizing members 308 are partially cylindrical and have a partially circular cross-sectional profile.

The distal ends of the stabilizing members 308 may have various shapes and configurations, as discussed above with respect to the stabilizing member embodiments of FIGS. 11A-11D. For example, in some embodiments, one or more of the stabilizing members 308 have a distal end with a rectangular configuration, triangular configuration, rounded configuration, or partially rounded configuration. In some embodiments, one or more of the stabilizing members 308 have a distal end with a plurality of teeth. In some embodiments, one or more of the stabilizing members 308 have a distal end with a textured configuration (e.g., a plurality of raised portions or bumps, etc.).

In some embodiments, the stabilizing members 308 are arranged in a pattern. However, in other embodiments, the stabilizing members 308 may have a somewhat random arrangement. Typically, at least one stabilizing member 308 is located near each of the first and second light guides 304, 306 to facilitate stabilization of the first and second light guides 304, 306 relative to the skin of a subject wearing the device 200.

Figure 13B:
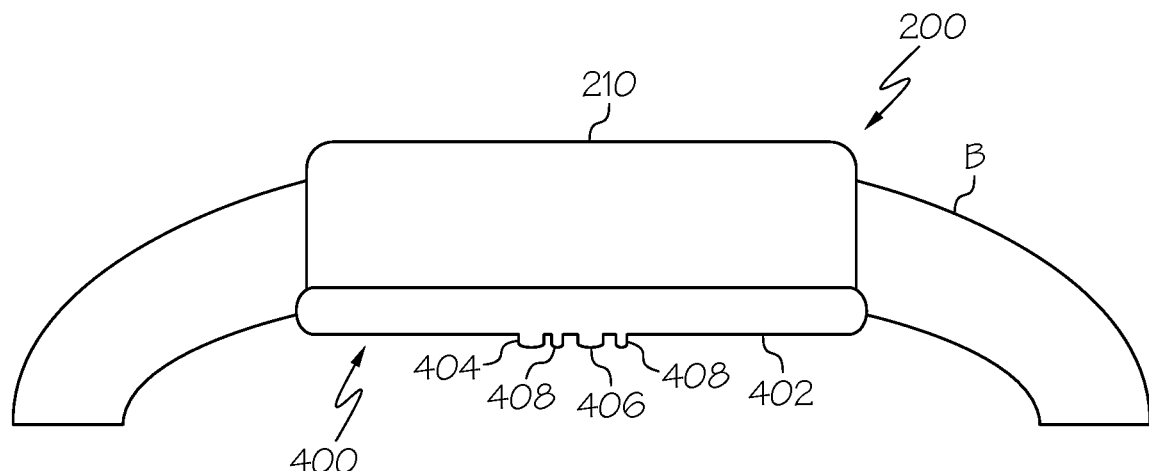
FIG. 13B illustrates an optical adapter secured to a wearable monitoring device having an optical sensor module, according to some embodiments of the present invention.

In FIG. 13B, an optical adapter 400, according to some embodiments is secured to the housing portion 210a of the monitoring device 200 of FIGS. 2A-2C. Similar to the base 302 of FIG. 13A, the adapter 400 includes a base 402 that is removably secured to the housing portion 210a, first and second light guides 404, 406 extending outwardly from the base 402, and a plurality of stabilizing members 408 extending outwardly from the base 402. The base 402 is different from the base 302 of the adapter 300 of FIG. 13A in that the base 402 is secured to substantially the entire housing portion 210a.

Optical adapters according to embodiments of the present invention may have various configurations. Exemplary embodiments are illustrated in FIGS. 14A-14B, 15A-15B, 16A-16B, and 17. The optical adapter 300 illustrated in FIGS. 14A-14B is a molded optical adapter wherein the base 302, first and second light guides 304, 306, and the stabilizing members 308 are formed from the same material. As illustrated in FIGS. 14B, 15B and 16B, the optical adapter 300, according to some embodiments, has a resilient peripheral lip (indicated by dashed line 307) on the outside of the optical adapter 300 that is configured to at least partially surround the peripheral edge of a device to which the optical adapter 300 is to be attached, such as a watch, etc., and secure the optical adapter 300 to the device.

The optical adapter 300 of FIGS. 15A-15B has a co-molded structure wherein the base 302 and stabilizing members 308 are formed from the same material and the first and second light guides 304, 306 are formed from a different material than the stabilizing members 308. It should be understood that an overmolded structure may also be used, such as wherein the light guiding material is overmolded on top of the base. In such an embodiment, it may be necessary to remove excess light-guiding material that may form across the surface of the base to help reduce optical crosstalk between the optical emitter and optical detector elements. That is, as generally used herein, a co-molded structure refers to a multi-component structure generated by industrially available molding methods. The multiple components may be different materials (such as optically transmissive light guides versus opaque bases or covers) or may be different expressions of the same material (such as colors or dyes of the same material).

In some embodiments, the stabilizing members 308 may be comprised of dissimilar materials, and the light guides 304, 306 may be comprised of dissimilar materials. One functional benefit of using stabilizing members 308 comprised of different materials is that each material may be optimized for a particular mechanical characteristic. For example, if some stabilizing members 308 are comprised of soft material and some stabilizing members 308 are comprised of hard material, both kinetic and static friction against the skin may be optimized more independently than if all stabilizing members 308 were comprised of one type of material. Thus, both mechanical stabilization and user comfort may be engineered into the optical adapter 300.

Similarly, having light guiding material for the optical emitter that is different than light guiding material for the optical detector may be useful in, somewhat independently, optimizing optical coupling and rejecting unwanted light scatter. For example, it may be advantageous to use light guides having different refractive indices for an optical emitter than for an optical detector, to encourage light guiding from the optical emitter into the skin but to prevent unwanted specular reflection from the skin from entering the detector optics. For example, in some embodiments, the emitter light guide may have a higher refractive index than the detector light guide. In general, an important property of the light guiding material for the optical emitter may be to guide light into the blood vessels through the skin; however, the an important property of the light guiding material for the optical detector may be to guide light scattered by the blood vessels (below the surface of the skin) and to reject light scattered by the skin surface (and other tissue) that does not contain blood flow information.

The optical adapter 300 illustrated in FIGS. 16A-16B is a molded optical adapter wherein the base 302, first and second light guides 304, 306, and the stabilizing members 308 are formed from the same material, and wherein internal features are also formed. The internal features may be designed to mate with the optics of the optical emitter(s) and/or detector(s). For example the optical emitter(s) and detector(s) may have various features associated with light-guiding and lensing, such as rounded optics, and coupling light to/from the body may be more effective with internal features that are designed to mate with the emitter and detector features. In contrast, the design of FIG. 14A-14B may be more suited for featureless emitter and detector optics (such as flat optics). Namely, the design of FIG. 14A-14B may be more suited for the base resting against a flat window wherein the optical emitter(s) and detector(s) are below the window (such as the embodiment of sensor 212 illustrated in FIG. 2).

Figure 17A:
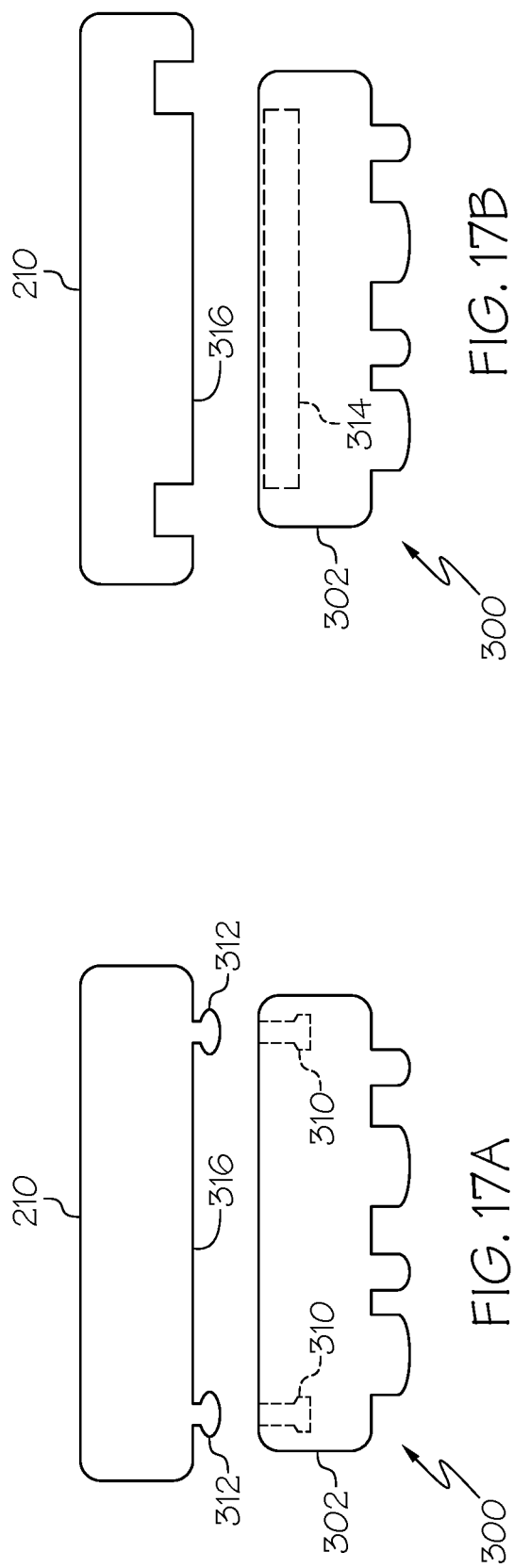
FIGS. 17A-17C are side views of optical adapters, according to embodiments of the present invention, and illustrating various ways of removably securing the optical adapters to a monitoring device.
Figure 17B:
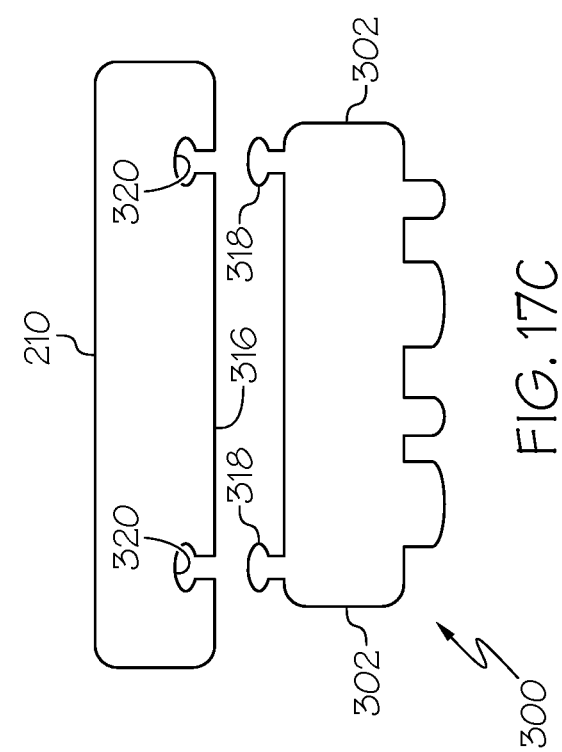
Figure 17C:

FIGS. 17A-17C are side views of multiple optical adapters 300, according to embodiments of the present invention, and illustrating various nonlimiting ways of removably securing the optical adapters 300 to a monitoring device. In FIG. 17A, the optical adapter 300 includes female connectors 310 in the base 302 that are configured to engage respective male connectors 312 extending from the biometric sensor housing 210. In FIG. 17C, the optical adapter 300 includes male connectors 318 extending from the base 302 that are configured to engage respective female connectors 320 in the biometric sensor housing 210. In FIG. 17B, the optical adapter 300 includes a recessed portion 314 configured to matingly engage an outwardly extending member 316 on the biometric sensor housing 210.

Referring now to FIGS. 18A-18D, an earbud cover 500, according to some embodiments of the present invention, is illustrated. The earbud cover 500 is configured to fit over the housing 901 of earbud 900. The illustrated earbud 900 includes two sensor modules 700 that are configured to direct energy towards the ear and detect an energy response from the ear. However, the earbud cover 500 may be utilized with earbuds having a single sensor module and with earbuds having more than two sensor modules. The illustrated earbud 900 also includes a supporting arm 902 connected to the earbud housing 901 to support a wire, electrical connections, and/or provide additional support around the ear. For example, the supporting arm 902 may be used to house wires or wrapped around the ear to further support the earbud housing 901 within the ear. However, earbud covers according to embodiments of the present invention may be utilized with earbuds not having a supporting arm. It should be noted that, although FIGS. 18A-18D are shown without ear clips, ear hooks, or other ear support features designed to help keep the earbud 900 within the ear during exercise, these features may be added to the earbud 900. However, these features are not required.

The illustrated earbud 900 also includes lenses (or light guides) 715 that at least partially encapsulate the emitters 44 and detectors 46 of the sensor modules 700. However, earbud covers 500 according to embodiments of the present invention may be utilized with earbuds not having such lenses.

Figure 18A:
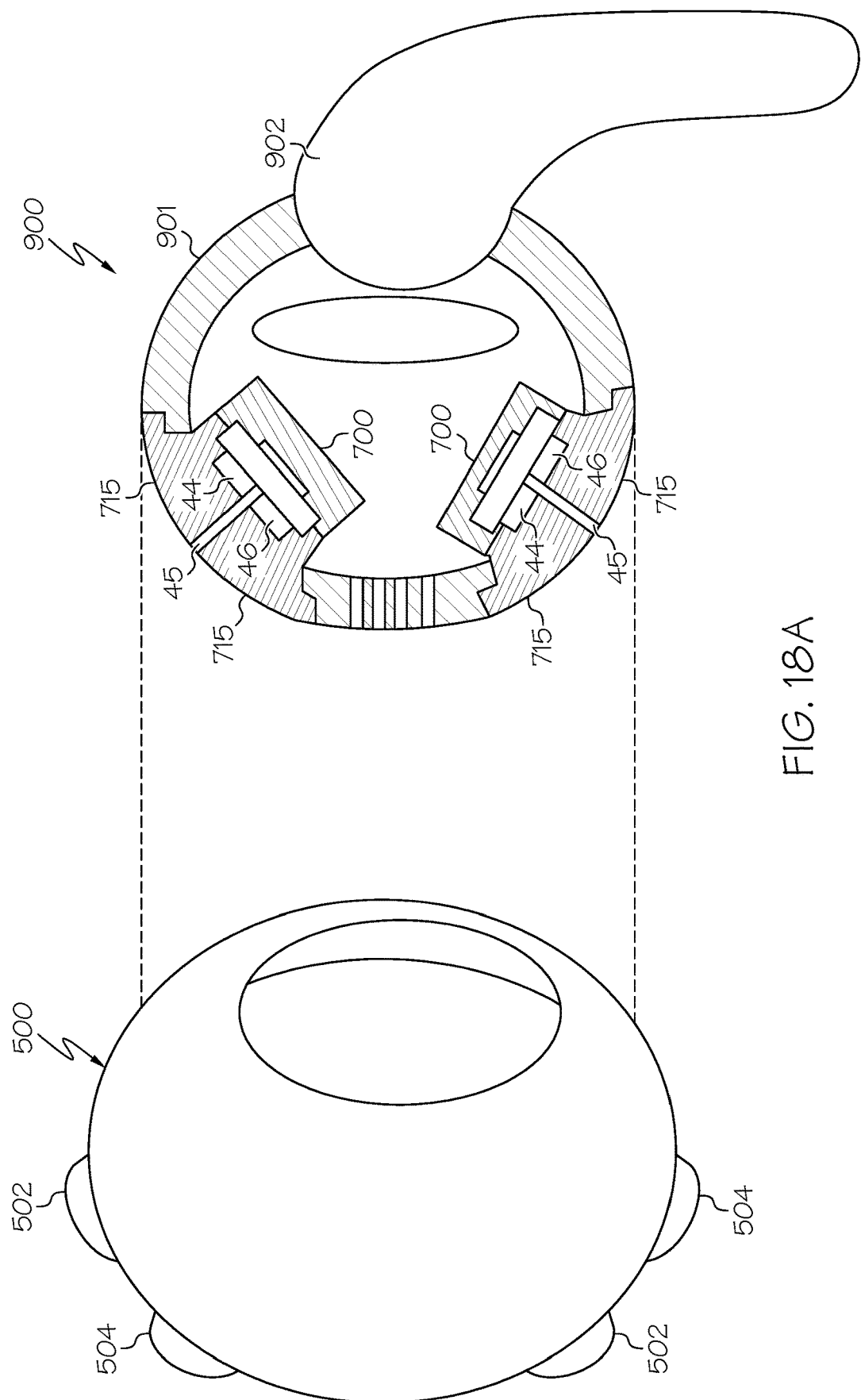
FIGS. 18A-18D illustrate a cover for an earbud, according to some embodiments of the present invention.
Figure 18B:
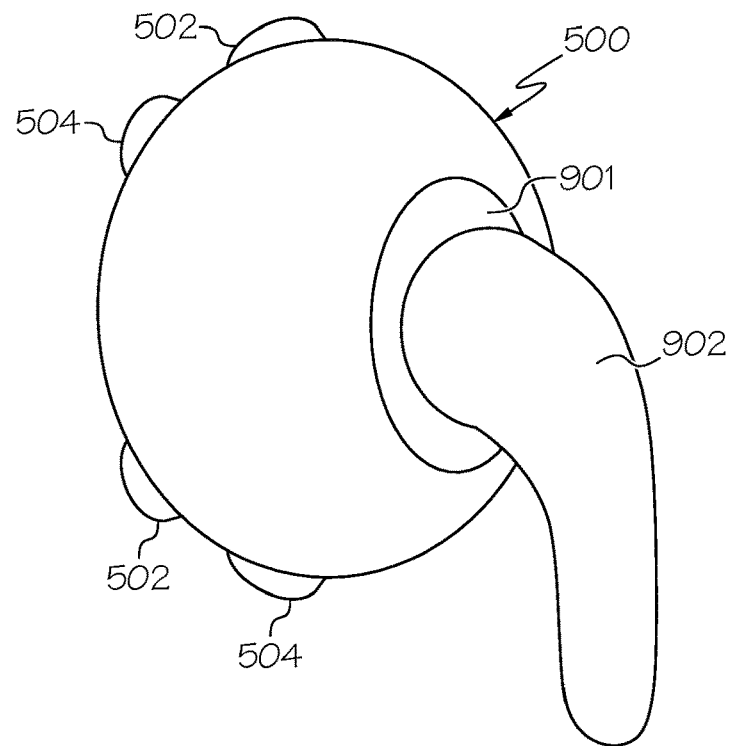
Figure 18C:
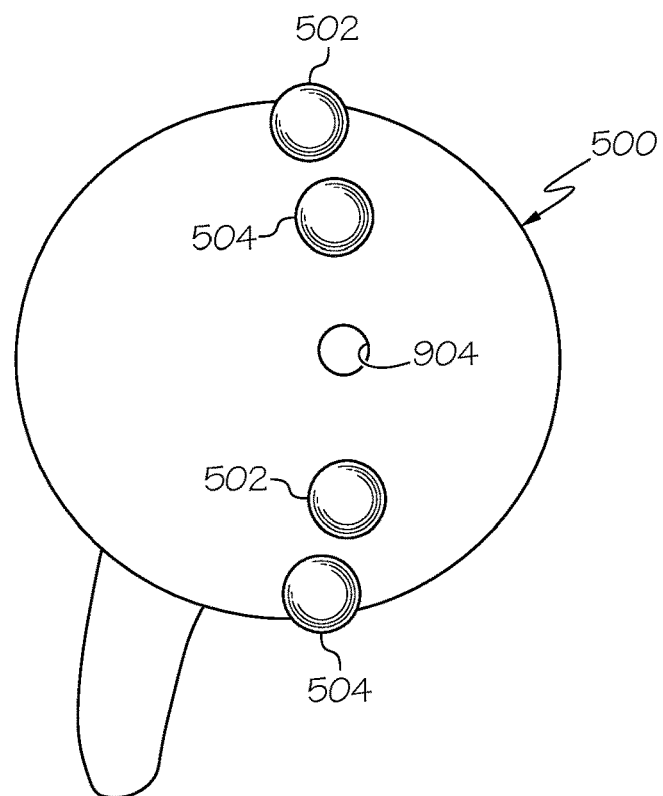
Figure 18D:
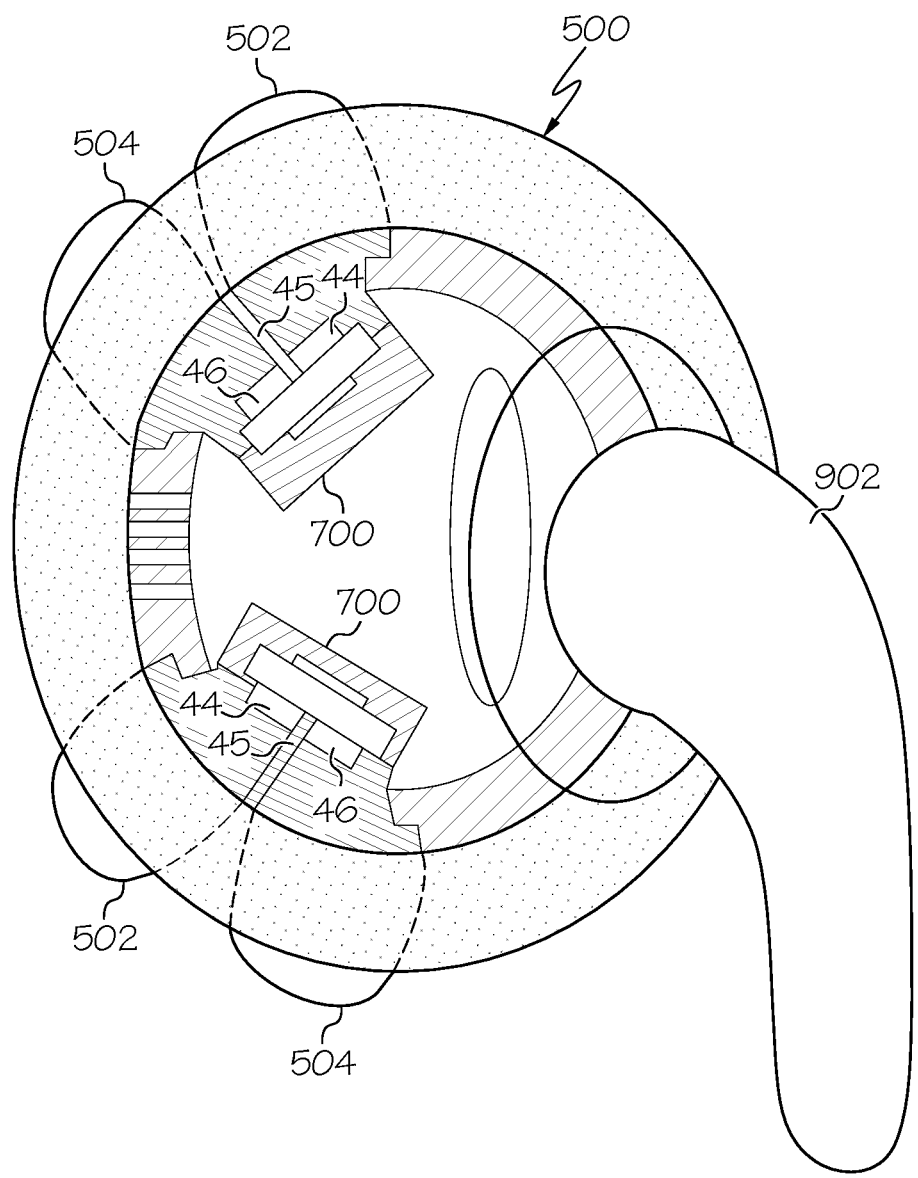

FIGS. 18B-18D illustrate the earbud cover 500 secured around the earbud housing 901. The illustrated earbud cover 500 includes a first light guide 502 that is configured to guide light from at least one optical emitter 44 associated with a sensor module 700 of the audio earbud to a region of a body of a subject wearing the audio earbud 900, and a second light guide 504 that is configured to guide light from the body of the subject to at least one optical detector 46 associated with a sensor module 700 of the audio earbud 900. The first and second light guides 502, 504 may be co-molded with the earbud cover 500. The illustrated earbud cover 500, and the barrier region 45 between the optical emitter 44 and optical detector 46 of the sensor module 700, is formed from an opaque material that is sufficiently opaque to prevent cross-talk between the emitter optics and the detector optics (i.e., between the emitter 44 and detector 46 themselves, and between the first and second light guides 502 and 504). In some embodiments, the earbud cover 500 includes a sound port 904 to facilitate sound passing therethrough from a speaker in the earbud 900 to an ear of a subject.

The first and second light guides 502, 504 comprise sufficiently optically transparent material having an index of refraction substantially greater than that of air, and are configured to direct light into the skin of a subject and collect light from the skin of a subject. As described above exemplary materials for the first and second light guides 502, 504 include, but are not limited to, plastic, polymer (such as polyurethane, rubber, polychloroprene, polyamides, polyesters, acrylics, silicone, polyethylene, polyphosphonates, polypropylene, poly(vinyl chloride), and polystyrene or the like), glass, epoxy, crystalline material, or an optically filtering material (such as materials comprising optical dyes, quantum dots, optical interference filters, or the like), etc.

The light guides 502, 504 (as well as light guides in other embodiments described herein), may additionally comprise an optical cladding region surrounding the long-axis of the optical light guides to facilitate light-guiding along the long-axis from the optical emitter to the body or the body to the optical detector. The material composition of this cladding material may comprise material having a lower index of refraction than the material of the light guides. Metals, metallics, semi-metals, and low-index polymers and glasses are non-limiting examples of potential cladding materials that may be used.

It should be noted that although the position of the emitter-detector optics is illustrated with the emitter optics (i.e., emitter 44 and first light guide 502) on the top and the detector optics (i.e., detector 46 and the second light guide 504) on the bottom, these positions may be switched. Moreover, the emitter and detector optics may be located in various positions throughout the earbud, as long as the positions enable sufficient proximity to the skin of the ear region of the user and as long as the mechanical stability of the earbud is supportive enough to prevent substantial movement of the optics with respect to the skin of the user.

Figure 19A:
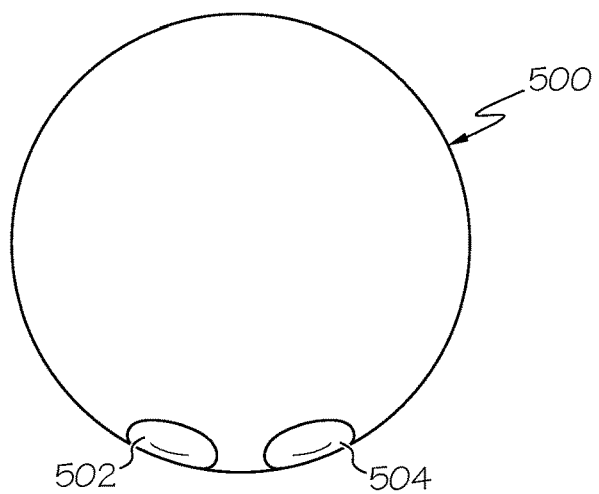
FIGS. 19A-19B illustrate a cover for an earbud, according to some embodiments of the present invention.
Figure 19B:
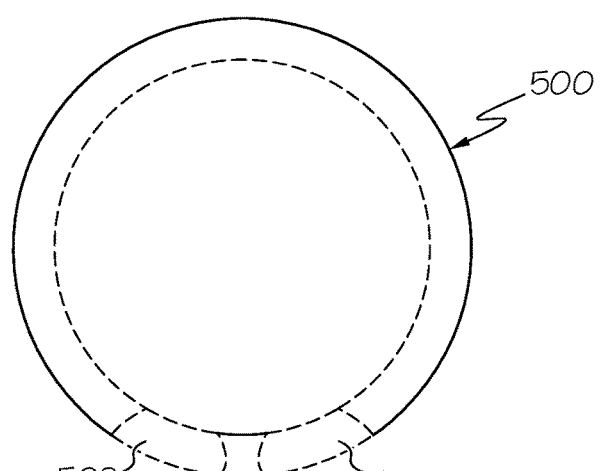

FIGS. 19A-19B illustrate an earbud cover 500 wherein the light guides 502, 504 are substantially flush with an outer surface of the earbud cover 500. Whereas extended light guides 502 and 504, as illustrated in FIGS. 18A-18D, may be more suited for optomechanical coupling between the body of a person and the optics of the earbud, flush light guides may be more comfortable for the user.

The thickness of the earbud cover 500 in FIGS. 18A-18D and 19A-19B may be between about 0.2 mm and about 6 mm to help support the earbud housing 901 within the ear of a person and without being too thick to fit in the ear. Thicker or thinner covers may be used, however.

Figure 20:
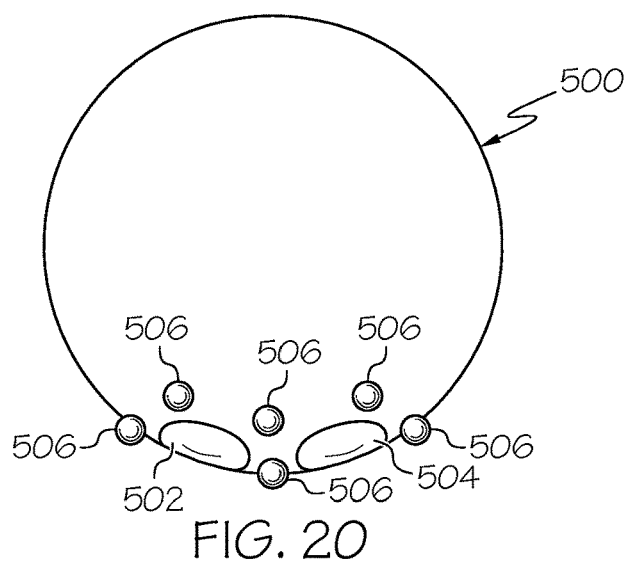
FIG. 20 illustrates a cover for an earbud, according to some embodiments of the present invention.
Figure 21A:
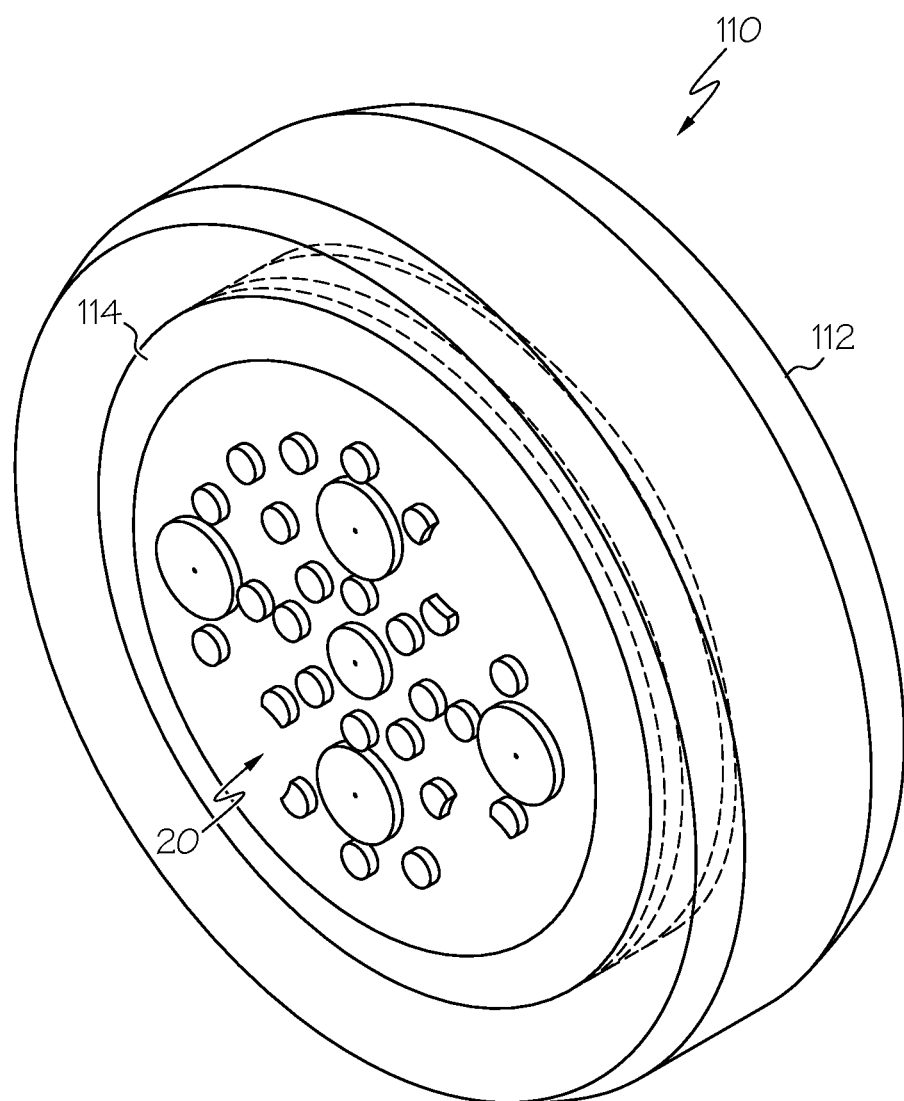
FIG. 21A is a perspective view of a wearable apparatus housing having the sensor module of FIG. 3 secured therewithin, according to some embodiments of the present invention.
Figure 21B:
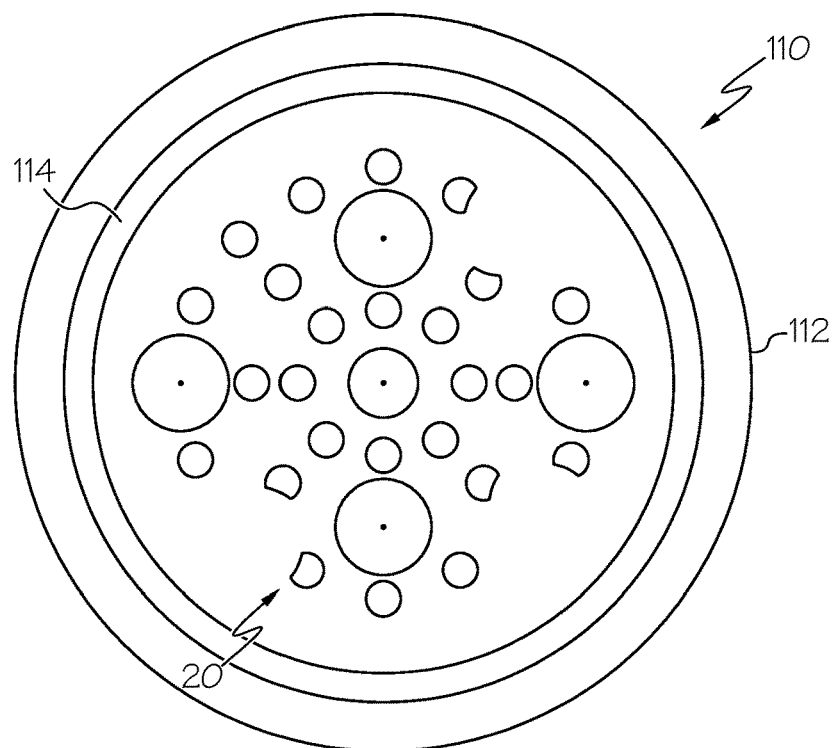
FIG. 21B is a bottom plan view of the wearable apparatus of FIG. 21A.
Figure 21C:
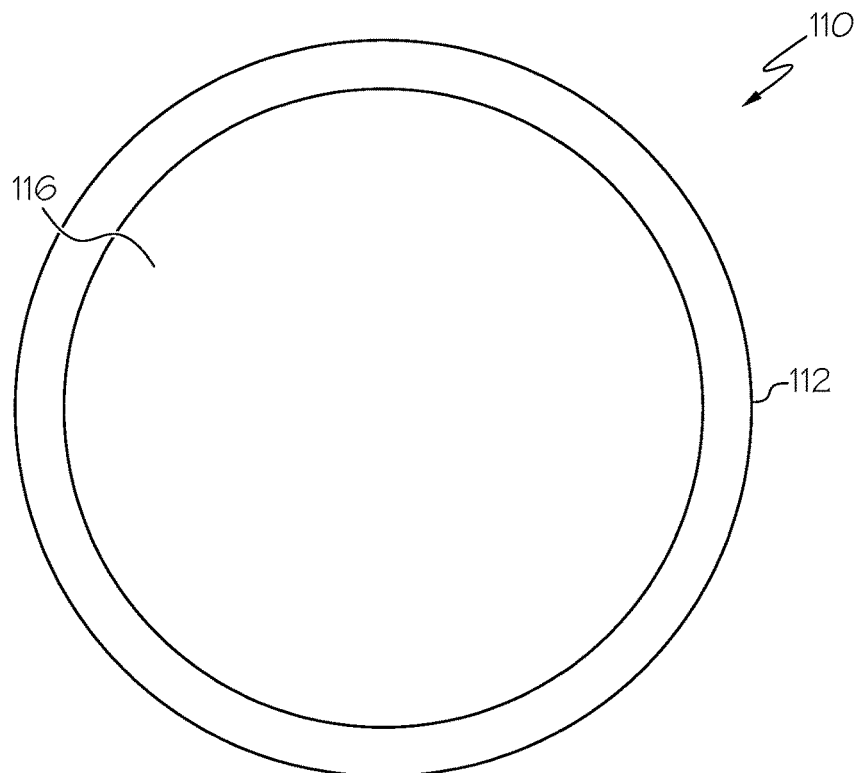
FIG. 21C is a top plan view of the wearable apparatus of FIG. 21A.
Figure 21D:
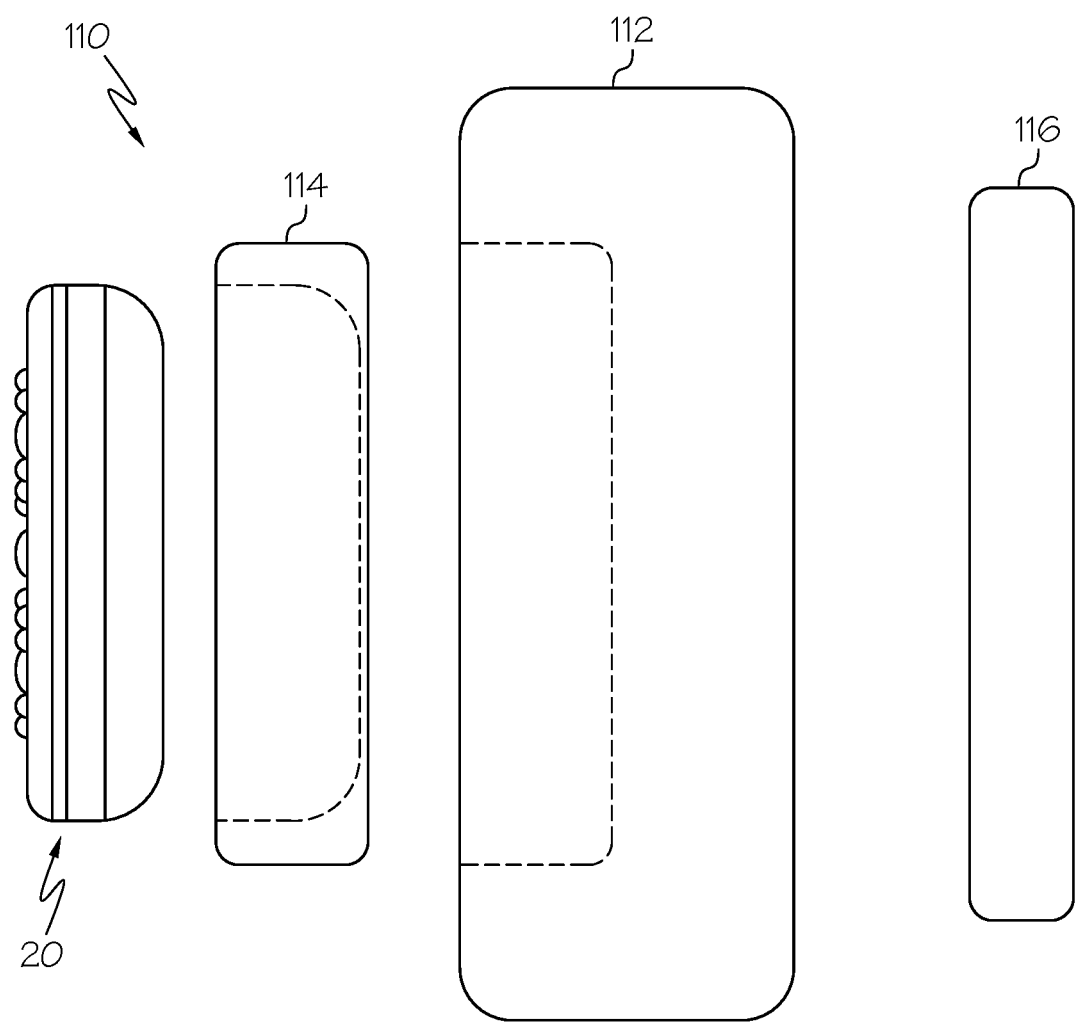
FIG. 21D is an exploded view of the wearable apparatus of FIG. 21A.

FIG. 20 illustrates an earbud cover 500 having a plurality of stabilizing members 506 extending outwardly from an outer surface of the cover 500 and adjacent the first and second light guides 502, 504. The stabilizing members 506 are typically formed from a resilient material. As described above, the stabilizing members 506 have a configuration and spacing that stabilizes the device around the skin region for energy interrogation (such as optical interrogation when the energy emitter is an optical emitter) without pushing away blood from the interrogation region (i.e., the skin region facing the energy emitter(s) and/or energy detector(s)).

As described above in previous embodiments, the stabilizing members 506 may be formed from resilient material, such as silicone, polymeric material, rubber, soft plastic, other elastomeric materials, or other compressible materials. However hard materials such as acrylic, hard plastic, hard polymeric material, glass, polycarbonate, metal, and the like may also be used. Various shapes, configurations, and materials may be utilized to implement the stabilizing members 506, without limitation. In some embodiments, the stabilizing members 506 may have a durometer range from about 10 (Type OO—ASTM D2240) to 80 (Type A—ASTM D2240), and a hardness range of about 20-50 Shore A, for example.

In some embodiments, at least some of the stabilizing members 506 are substantially cylindrical and have a substantially circular cross-sectional profile, and at least some of the stabilizing members are partially cylindrical and have a partially circular cross-sectional profile. Other cross-sectional shapes, such as triangular, rectangular, or the like, may be used, also. The stabilizing members 506 may be arranged in a pattern. However, in other embodiments, the stabilizing members 506 may have a somewhat random arrangement.

In some embodiments, one or more of the stabilizing members 506 have a distal end with a rounded configuration, as described above with respect to FIG. 11A. In some embodiments, one or more of the stabilizing members 506 have a distal end with a textured configuration, such as a plurality of raised bumps, as described above with respect to FIG. 11D. In some embodiments, one or more of the stabilizing members 506 have a distal end with a plurality of teeth, as described above with respect to FIG. 11C.

In some embodiments, the earbud cover 500 is formed from plastic, polymer, or silicone, and the first and second light guides 502, 504 are formed from plastic, polymer, silicone, acrylic, glass, polycarbonate, or an optically filtering material.

FIGS. 26 and 27A-27H illustrate a sensing device 800 configured to be worn in an ear of a subject, according to other embodiments of the present invention. The sensing device 800 of FIGS. 26 and 27A-27H is different from the earbud device 900 of FIGS. 18A-18D, 19A-18B and 20 in that device 800 is configured to be inserted inside the ear canal 1000. In contrast, the earbud device 900 of FIGS. 18A-18D, 19A-18B and 20 is configured to engage primarily the concha and anti-tragus region of an ear of a subject.

The illustrated sensing device 800 of FIGS. 26 and 27A-27H includes a body or housing 802 having a distal end portion 803 and a light-guiding ear tip or cover 804 (that is similar to the light guiding earbud cover 500 of FIGS. 18A-18D) that is configured to be inserted over the distal end portion 803. The illustrated cover 804 includes a light-guide 502 for guiding light from at least one optical emitter in the sensing device 800 to at least one region of the ear canal and a light-guide 504 for guiding light to at least one optical detector in the sensing device 800 from at least one region of the ear canal. However, in other embodiments, the sensing device 800 may have multiple light guides 502 for guiding light from at least one optical emitter in the sensing device 800 to at least one region of the ear canal. In addition, in other embodiments, the sensing device 800 may have multiple light-guides 504 for guiding light to at least one optical detector in the sensing device 800 from at least one region of the ear canal. The illustrated sensing device also includes a plurality of stabilizing members 506 extending from the light-guiding cover 804 and configured to stabilize the sensing device 800, as described above. In the illustrated embodiment, there are three stabilizing members 506. However, various numbers of stabilizing members 506, including a single stabilizing member 506, may be utilized.

Figure 27A:
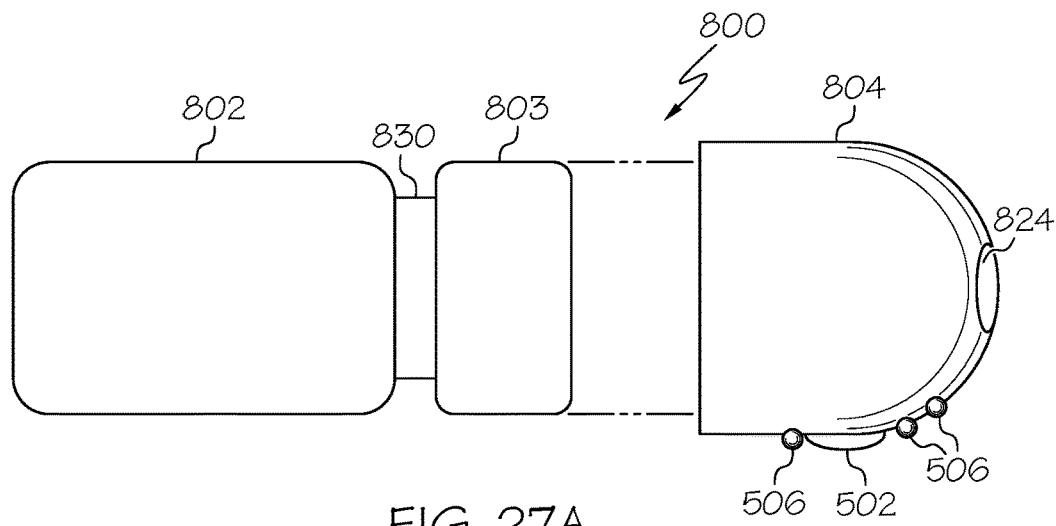
FIG. 27A is an exploded view of the sensing device of FIG. 26.
Figure 27B:
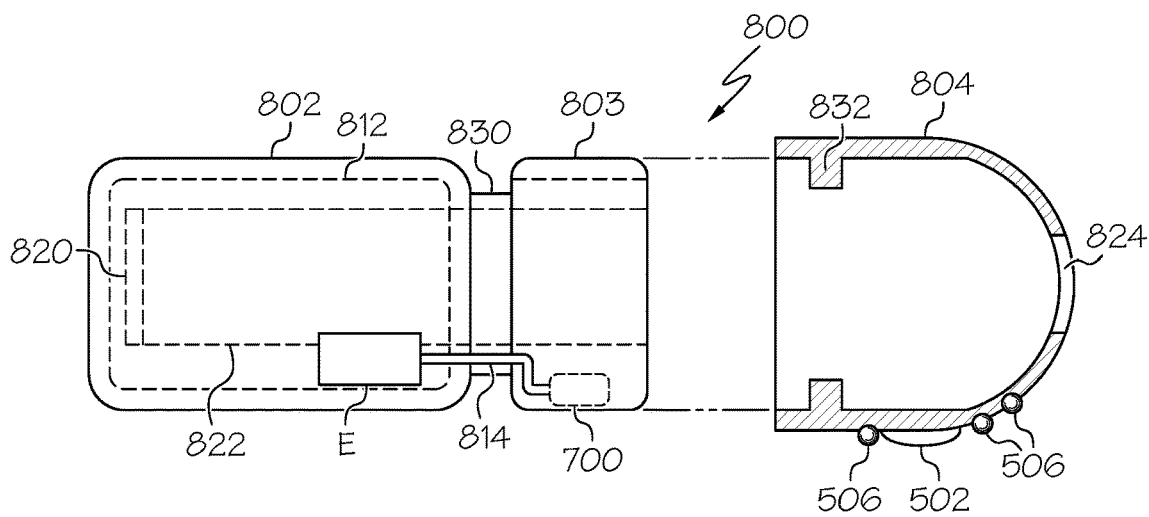
FIG. 27B is an exploded cross-sectional view of the sensing device of FIG. 26.

Referring to FIG. 27B, an optical sensor module 700, similar to optical sensor module 700 of FIGS. 18A-18D, is located in the housing 802, and includes one or more optical emitters and one or more optical detectors (not shown). However, other configurations are possible, and the optical emitter(s) and detector(s) do not need to be configured in a module.

Referring back to FIG. 26, the illustrated in-ear sensing device 800 includes an ear support fitting 810 at least partially surrounding a portion of the housing 802 that is configured to help mechanically support and stabilize the in-ear sensing device 800 within the ear canal. Multiple ear support fittings 810 may be utilized in accordance with embodiments of the present invention. The ear support fitting 810 may be constructed from various materials including resilient materials and rigid materials, and may have various shapes and configurations.

In some embodiments, the in-ear sensing device 800 may have the form-factor of a hearing aid, audio earpiece, earplug, smart earpiece, or the like, and the in-ear sensing device 800 may share functionality as both a sensor device and a personal communicator or smart computer. However, other form-factors may be used. The housing 802 may support various electrical elements (referred to generally as E in FIGS. 27B-27C), such as the electronics and circuit board(s) required for optical (PPG) sensing, telemetry of PPG data to a remote device, audio communication electronics (such as a microphone and/or speaker), a power source, powering electronics for remote charging or powering, at least one microprocessor for processing signals and/or controlling electronics, digital and/or analog controls for controlling sensor and/or audio functionality, and the like. The housing 802 may comprise a component support region 812 (FIG. 27B) inside the housing 802 for supporting these electronic elements, but electronic elements may be located in various other locations of the in-ear sensing device 800. For example, an electrical connection 814 may be located between the component support region 812 and the distal end portion 803 of the housing 802 for powering and/or controlling the optical emitter and detector components of the sensor module 700.

One function of the light-guiding cover 804 is to help optically couple the emitter and/or detector of the sensor module 700 to the skin of the ear canal and hence the blood flow below the skin. Another function of the cover 804 is help couple sound or other energy to the ear for audio communication. The in-ear sensing device 800 may include an acoustic driver 820 and an acoustic pathway 822 in the housing 802 that is in communication with an acoustic opening 824 in the cover 804. This same acoustic pathway 822 may be used to couple sound from the ear to a microphone in the housing 802. However, it should be understood that other acoustic communication devices and methods may be used in accordance with embodiments of the present invention.

Figure 27C:
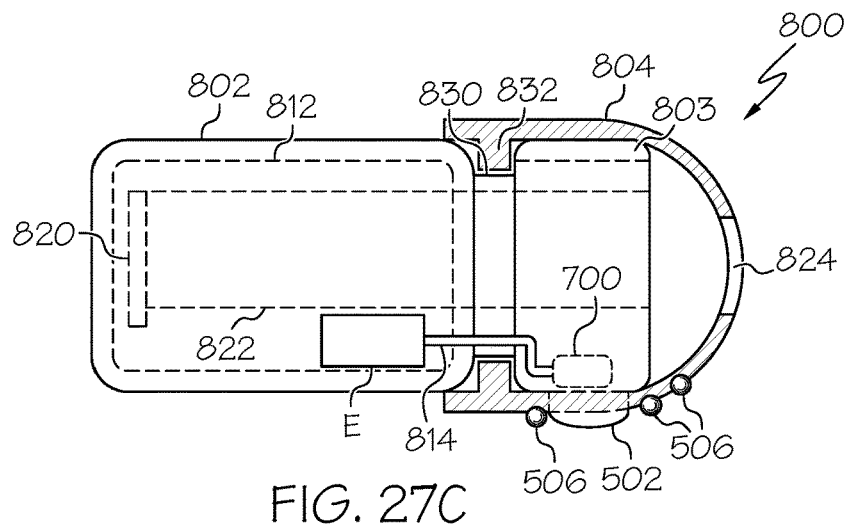
FIG. 27C is an assembled cross-sectional view of the sensing device of FIG. 26.

As shown in FIGS. 27A-27C, the cover 804 may be configured to slide and lock onto the distal portion 803 of the housing 802 via a mating connection. For example, in the illustrated embodiment, a recessed or female portion 830 is formed circumferentially in the housing 802 adjacent the distal end portion 803. The cover 804 includes a circumferentially extending (or partially circumferentially extending) protrusion or male portion 832 that is configured to matingly engage the female portion 830 and secure the cover 804 to the distal end portion 803, for example, as a snap fit. In other embodiments, the male and female portions may be reversed. For example, a recessed or female portion may be formed circumferentially in the cover 804, and the housing 802 may have a circumferentially extending male portion adjacent the distal end portion 803 that is configured to matingly engage the female portion and secure the cover 804 to the distal end portion 803. Moreover, embodiments of the present invention are not limited to the illustrated male-female connector structure for securing the cover 804 to the distal end portion 803. Various other ways of securing the cover 804 to the distal end portion 803 may be utilized.

Figure 27D:
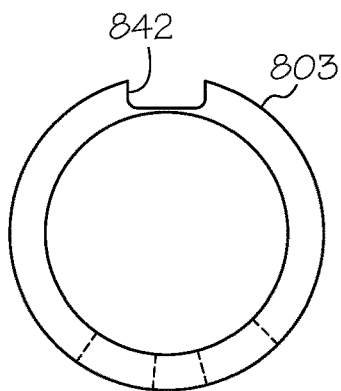
FIG. 27D illustrates the distal end portion of the sensing device of FIG. 26 without the cover secured to the housing.
Figure 27E:
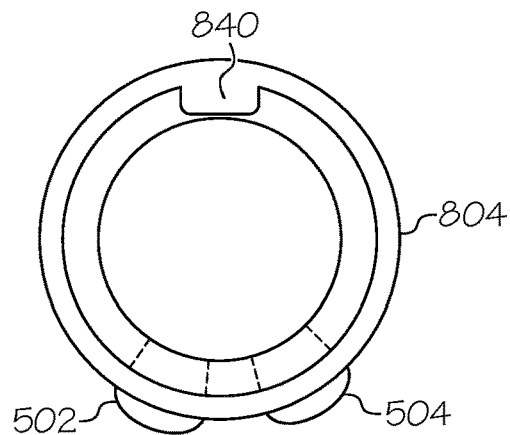
FIG. 27E is illustrates the distal end portion of the sensing device housing of FIG. 26 with the cover secured thereto, but with the cover shown in cross-section so as to illustrate the alignment tab of the cover engaged with the recess in the distal end portion of the housing.

In the illustrated embodiment of FIGS. 27D-27E, an alignment tab 840 is also associated with the cover 804 and is configured to engage a slot or recess 842 formed in the distal end portion 803. FIG. 27D illustrates the distal end portion 803 without the cover 804 secured thereto and FIG. 27E illustrates the distal end portion 803 with the cover 804 secured thereto. The mating connection of the cover 804 to the distal end portion 803 via the alignment tab 840 and recess 842 may help assure appropriate alignment of the cover 804 on the housing 803 such that optics (i.e., optical emitter(s) and detector(s)) in the sensor module 700 are aligned with the light-guide(s) 502, 504 each time the cover 804 is placed on the distal end portion 803.

Figure 27F:
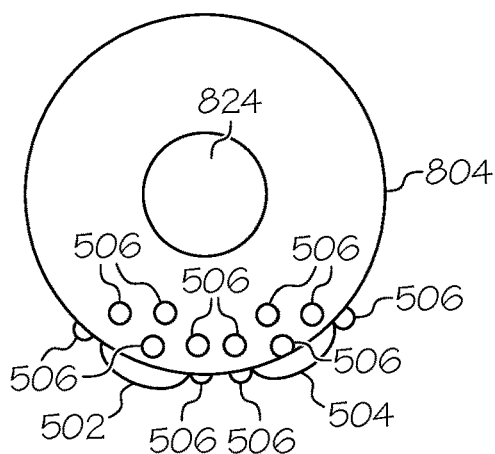
FIG. 27F is a front view of the cover of the sensing device of FIG. 26.
Figure 27G:
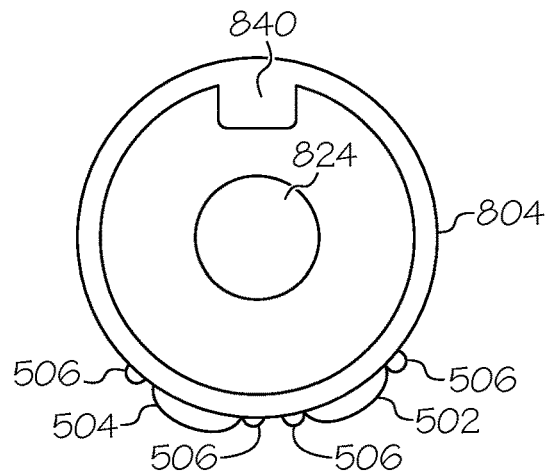
FIG. 27G is a rear view of the cover of the sensing device of FIG. 26.

FIG. 27F is a front view of the cover 804 and FIG. 27G is a rear view of the cover 804. As illustrated in FIGS. 27F-27G, a plurality of stabilizing members 506 may be utilized.

Figure 27H:
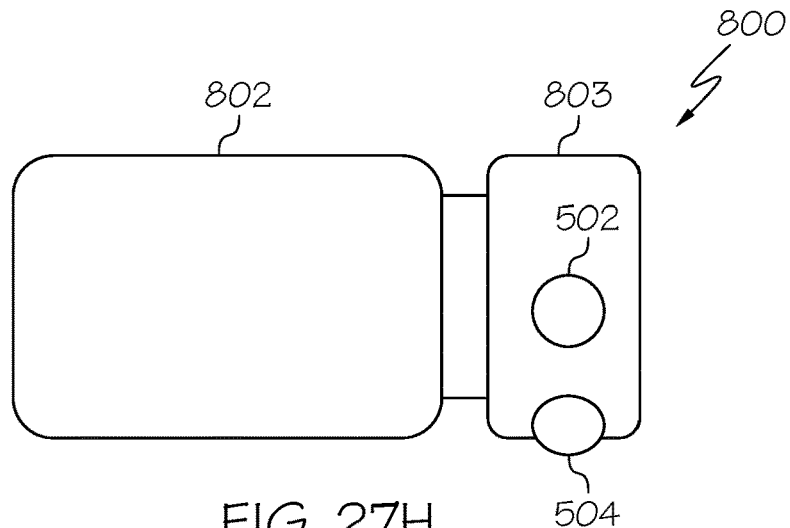
FIG. 27H is a side view of the housing of the sensing device of FIG. 26, according to other embodiments of the present invention, and wherein at least one light guide is integrated within the housing.

It should be noted that in some embodiments, the light guides 502, 504 may be protrusions from the cover 804 with distal ends that guide light directly between the skin of the ear and the optics (i.e., optical emitter(s) and detector(s)) in the sensor module 700. In other embodiments, the light guides 502, 504 may be integrated within the distal end portion 803 and not integrated within the cover 804, itself, as illustrated in FIG. 27H. In such case, there may be respective aligned holes or apertures in the cover 804 to allow the light guides 502, 504 to pass through (or to guide light through but not necessarily extend through) as the cover 804 is placed on the distal end portion 803. In some embodiments, there may be a single hole or aperture through which both light guides 502, 504 can pass through (or to guide light through but not necessarily extend through). In some embodiments, there may be a single light guide 502 (and corresponding aperture in the cover 804) for guiding light from at least one optical emitter in the sensing device 800. In other embodiments, there may be a single light guide 504 (and corresponding aperture in the cover 804) for guiding light to at least one optical detector in the sensing device 800. Moreover, nothing in this description should be construed to limit the number of light guides and location of light guides that may be integrated within the cover 804 or within the distal end portion 803 or housing 802 of the sensing device 800.

The housing 802, cover 804, and the ear support fitting 810 may be formed from virtually any solid material that can support compression within the ear and which does not irritate the skin of a user, such as metal, wood, rubber, plastic, polymer-based material, glass, or the like. In some embodiments, the cover 804 and support fitting 810 are formed of softer, more pliable material than the housing 802, such that the cover 804 and support fitting 810 are compressed more than the housing 802, balancing the mechanical forces, when the in-ear device 800 is placed in the ear. This can help prevent "fidgets" in the sensor readings as the optics of the sensor module 700 and associated light guides 502, 504 are displaced during abrupt or aggressive motion.

The stabilizing members 506 may be configured in the same manner as described previously, comprising the same materials as previously described. For example, the stabilizing members 506 may be formed from resilient material, such as silicone, polymeric material, rubber, soft plastic, other elastomeric materials, or other compressible materials. However hard materials such as acrylic, hard plastic, hard polymeric material, glass, polycarbonate, metal, and the like may also be used. Various shapes, configurations, and materials may be utilized to implement the stabilizing members 506, without limitation. In some embodiments, the stabilizing members 506 may have a durometer range from about 10 (Type OO—ASTM D2240) to 80 (Type A—ASTM D2240), and a hardness range of about 20-50 Shore A, for example.

As a specific example, the stabilizing members 506 illustrated in FIG. 20 and FIGS. 27A-27G may be integrated within the respective covers 500 and 804 via single-shot molding (for uniform material) or multi-shot molding (for the case where the cover material and stabilizing member material are different).

The light guides 502, 504 may also be configured in the same manner as previously described, comprising the same materials as previously described. For example, the light guides 502, 504 comprise sufficiently optically transparent material having an index of refraction substantially greater than that of air, and are configured to direct light into the skin of a subject and collect light from the skin of a subject. As described above exemplary materials for the light guides 502, 504 include, but are not limited to, plastic, polymer (such as polyurethane, rubber, polychloroprene, polyamides, polyesters, acrylics, silicone, polyethylene, polyphosphonates, polypropylene, poly(vinyl chloride), and polystyrene or the like), glass, epoxy, crystalline material, or an optically filtering material (such as materials comprising optical dyes, quantum dots, optical interference filters, or the like), etc.

In some embodiments, the light guides 502, 504 may be co-molded with the cover 804 or co-molded with the housing 802 and distal end portion 803, such that the light guides 502, 504 comprise optically transmissive material and the cover material comprises optically opaque material. Preferably, the optically opaque material utilized would block more than about 70% of external light (such as ambient light or sunlight) covering the wavelength range from about 200 nm to about 1200 nm, if the optical detector of the sensor module 700 is a silicon-based detector. As a specific example, this blocking power is achievable with black-dyed plastics, rubbers, elastomeric materials, and silicon. For the case of an infrared-based optical emitter, the light guides 502, 504 may additionally be comprised of a dye or other optical filtering material that selectively passes infrared light and rejects visible light. Dyed glasses, dyed polycarbonates, and dyed acrylics are non-limiting examples of suitable filtering materials. Particularly well-suited infrared-passing dye material may be Gentex Corporation E800 or other optically absorptive dyes.

It should be noted that although the figures herein may show a certain limited number of emitters, detectors, stabilizing members, protrusions, light-guides, and the like, embodiments of the present invention can be utilized with a plurality of these elements in a wearable device.

It should be noted that a variety of energy emitters and energy detectors may be generally used within embodiments of the present invention such that mechanical stabilization at the skin does not negatively affect blood flow (and thus the desired blood flow signal) below the emitter and detector. In such case the stabilizers may be essentially identical to that used for the case of optical emitters and optical detectors as described above, but the protrusions (energy guiding protrusions) may be substantially different. For example, for the case where the energy emitter is a thermal emitter, the emitter and detector protrusions may comprise a core of thermally conductive material (i.e., metals, metallics, conducting polymer materials, nanostructured materials, and the like) and a cladding of thermally insulating material (i.e., insulating polymers, insulating plastics, rubber, insulating polycarbonate, acrylic, insulating glass, etc.). For the case where electrical emitters and detectors are used, the emitter and detector protrusions may comprise a core of electrically conductive material and a cladding of electrically insulating material. In the case of a mechanical emitter (such as a piezoelectric actuator) and mechanical detector, the emitter and detector protrusions may be comprised of a mechanically rigid material and a cladding of mechanically resilient material. In all of these cases, cladding may not be critical for biometric sensing functionality, but may be supportive by directing energy transmission through the desired pathway between the body of the person and the emitter/detector. Moreover, a variety of electrically conductive materials, mechanically rigid materials, resilient materials, etc. may be used as is well-known to those skilled in the art.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. As an example, although many drawings in this invention have shown sensing elements located within the inner region of the ear, the invention could be applied to designs where the sensing element is configured to be placed on the outside of the ear, such as a location behind the earlobe or in front of the tragus. Accordingly, all such modifications are intended to be included within the scope of this invention as defined in the claims. The invention is defined by the following claims, with equivalents of the claims to be included therein.

That which is claimed is:

1. A sensor module, comprising:
    a housing comprising a portion that faces a subject when the sensor module is worn by the subject; and
    a sensor assembly disposed within the housing, the sensor assembly comprising:
    a base comprising at least one optical emitter and at least one optical detector; and
    a guide layer overlying the base in face-to-face relationship, wherein the guide layer comprises a surface, at least one protrusion extending outwardly from the guide layer surface, wherein the at least one protrusion is in optical communication with the at least one optical emitter and is configured to guide light into the subject wearing the sensor module, and a plurality of stabilizing members extending outwardly from the guide layer surface;
    wherein the housing portion comprises at least one first opening through which the at least one protrusion extends, and a plurality of second openings through which the stabilizing members extend.

2. The sensor module of claim 1, wherein at least some of the stabilizing members have an outwardly extending length that is greater than an outwardly extending length of the at least one protrusion.

3. The sensor module of claim 1, further comprising a lens overlying and in optical communication with the at least one optical detector, wherein the guide layer comprises an opening configured to accommodate the lens, and wherein the housing comprises a third opening through which the lens extends.

4. The sensor module of claim 1, further comprising a lens overlying and in optical communication with the at least one optical emitter.

5. The sensor module of claim 1, wherein at least some of the stabilizing members are substantially cylindrical and have a substantially circular cross-sectional profile, and wherein at least some of the stabilizing members are partially cylindrical and have a partially circular cross-sectional profile.

6. The sensor module of claim 1, wherein at least one of the stabilizing members has a distal end with a rounded configuration, a textured configuration, or a plurality of teeth.

7. The sensor module of claim 6, wherein the textured configuration comprises a plurality of raised bumps.

8. The sensor module of claim 1, wherein the stabilizing members are arranged in a pattern.

9. The sensor module of claim 1, wherein the base comprises a plurality of optical emitters, wherein the guide layer comprises a plurality of outwardly extending protrusions, each in optical communication with a respective one of the plurality of optical emitters, and wherein the housing portion comprises a plurality of first openings through which the protrusions extend.

10. The sensor module of claim 1, wherein the housing comprises a first magnet configured to removably secure the sensor module to a wearable article via a second magnet, wherein the wearable article is an earbud, an armband, a wristband, a legband, a neckband, a ring, jewelry, glasses, headgear, a patch, a tattoo, an earring, or an article of clothing.

11. A sensor module, comprising:
    a housing; and
    a sensor assembly disposed within the housing, the sensor assembly comprising at least one optical emitter, at least one optical detector, at least one protrusion in optical communication with the at least one optical emitter and configured to guide light into a subject wearing the sensor module, and a plurality of stabilizing members,
    wherein the at least one protrusion and the plurality of stabilizing members extend outwardly through a same portion of the housing that faces a subject when the sensor module is worn by the subject, and
    wherein at least some of the stabilizing members have an outwardly extending length that is greater than an outwardly extending length of the at least one protrusion.

12. The sensor module of claim 11, further comprising a lens overlying and in optical communication with the at least one optical emitter and/or optical detector.

13. The sensor module of claim 11, further comprising at least one of a signal processor configured to receive and process signals produced by the at least one optical detector, a motion sensor configured to detect motion of the sensor module, and a wireless transmitter configured to transmit data from the at least one optical detector to a remote device.

14. The sensor module of claim 11, wherein the housing is configured to removably receive a fastener for securing the sensor module to a wearable article, such as an earbud, an armband, a wristband, a legband, a neckband, a ring, jewelry, glasses, headgear, a patch, an earring, or an article of clothing.

15. The sensor module of claim 11, wherein the housing comprises a first magnet configured to removably secure the sensor module to a wearable article via a second magnet, wherein the wearable article is an earbud, an armband, a wristband, a legband, a neckband, a ring, jewelry, glasses, headgear, a patch, a tattoo, an earring, or an article of clothing.

16. A wearable apparatus for measuring one or more biometric parameters from a subject, wherein the apparatus is configured to be worn against the skin of a subject, the apparatus comprising:
    a housing comprising a portion that faces the skin of the subject when the apparatus is worn by the subject;
    at least one optical emitter within the housing;
    at least one optical detector within the housing;
    at least one first stabilizing member in proximity to the at least one optical emitter, the at least one first stabilizing member extending outwardly through the housing portion; and
    at least one second stabilizing member in proximity to the at least one optical detector, the at least one second stabilizing member extending outwardly through the housing portion;
    wherein the at least one first and second stabilizing members are configured to contact the skin of the user and stabilize movement of the at least one emitter and the at least one detector relative to the skin.

17. The wearable apparatus of claim 16, wherein the at least one optical emitter and at least one optical detector are supported by a base, wherein the at least one first stabilizing member has an outwardly extending length that is greater than a height of the at least one optical emitter relative to the base, and wherein the at least one second stabilizing member has an outwardly extending length that is greater than a height of the at least one optical detector relative to the base.

* * * * *